United States Patent
Mehra et al.

(10) Patent No.: US 11,254,789 B2
(45) Date of Patent: Feb. 22, 2022

(54) IONICALLY MODIFIED SILICONES, COMPOSITIONS, AND MEDICAL DEVICES FORMED THEREFROM

(71) Applicant: Momentive Performance Materials Inc., Waterford, NY (US)

(72) Inventors: Meenal Mehra, Bangalore (IN); Raveendra Mathad, Bangalore (IN); Shreedhar Bhat, Bangalore (IN)

(73) Assignee: Momentive Performance Materials Inc., Waterford, NY (US)

( * ) Notice: Subject to any disclaimer, the term of this patent is extended or adjusted under 35 U.S.C. 154(b) by 128 days.

(21) Appl. No.: 16/482,734

(22) PCT Filed: Feb. 16, 2018

(86) PCT No.: PCT/US2018/018476
§ 371 (c)(1),
(2) Date: Aug. 1, 2019

(87) PCT Pub. No.: WO2018/152392
PCT Pub. Date: Aug. 23, 2018

(65) Prior Publication Data
US 2020/0223985 A1    Jul. 16, 2020

Related U.S. Application Data

(60) Provisional application No. 62/459,632, filed on Feb. 16, 2017.

(51) Int. Cl.
| | |
|---|---|
| C08G 77/20 | (2006.01) |
| C08F 230/08 | (2006.01) |
| C08G 77/388 | (2006.01) |
| A61K 47/69 | (2017.01) |
| A61K 9/00 | (2006.01) |
| A61K 9/70 | (2006.01) |
| A61K 47/34 | (2017.01) |
| C08G 77/18 | (2006.01) |
| G02B 1/04 | (2006.01) |
| A61K 9/06 | (2006.01) |
| C08G 77/22 | (2006.01) |
| C08G 77/392 | (2006.01) |
| C09D 183/06 | (2006.01) |
| C08G 77/04 | (2006.01) |
| A61K 45/06 | (2006.01) |
| C08G 77/06 | (2006.01) |

(52) U.S. Cl.
CPC .......... *C08G 77/388* (2013.01); *A61K 9/0051* (2013.01); *A61K 9/06* (2013.01); *A61K 9/7023* (2013.01); *A61K 47/34* (2013.01); *A61K 47/6903* (2017.08); *C08F 230/08* (2013.01); *C08G 77/18* (2013.01); *C08G 77/20* (2013.01); *C08G 77/22* (2013.01); *C08G 77/392* (2013.01); *C09D 183/06* (2013.01); *G02B 1/043* (2013.01); *A61K 45/06* (2013.01); *C08G 77/045* (2013.01); *C08G 77/06* (2013.01); *C08G 2210/00* (2013.01)

(58) Field of Classification Search
CPC .............................. C08G 77/20; C08F 230/08
See application file for complete search history.

(56) References Cited

U.S. PATENT DOCUMENTS

| | | | |
|---|---|---|---|
| 4,260,725 A | 4/1981 | Koegh et al. | |
| 4,536,554 A | 8/1985 | Lim et al. | |
| 4,983,702 A | 1/1991 | Mueller et al. | |
| 5,087,392 A | 2/1992 | Burke et al. | |
| 5,352,714 A | 10/1994 | Lai et al. | |
| 5,536,861 A | 7/1996 | Robertson | |
| 5,656,210 A | 8/1997 | Hill et al. | |
| 5,998,498 A | 12/1999 | Vanderlaan et al. | |
| 6,013,711 A | 1/2000 | Lewis et al. | |
| 6,207,782 B1 | 3/2001 | Czech et al. | |
| 6,867,245 B2 | 3/2005 | Iwata et al. | |
| 7,557,231 B2 | 7/2009 | Schorzman et al. | |
| 7,601,766 B2 | 10/2009 | Schorzman et al. | |
| 7,732,546 B2 | 6/2010 | Salamone et al. | |
| 7,781,558 B2 | 8/2010 | Schorzman et al. | |
| 7,825,273 B2 | 11/2010 | Schorzman et al. | |
| 2007/0160643 A1* | 7/2007 | Schorzman | G02B 1/043 424/423 |
| 2008/0076898 A1* | 3/2008 | Salamone | C08G 77/30 528/26 |
| 2012/0136087 A1 | 5/2012 | Parakka et al. | |

(Continued)

FOREIGN PATENT DOCUMENTS

| | | |
|---|---|---|
| JP | 2016053165 A | 4/2016 |
| JP | 2017512879 A | 5/2017 |

OTHER PUBLICATIONS

Patent Cooperation Treaty (PCT), International Search Report and Written Opinion for Application PCT/US2018/018476 filed Feb. 16, 2018, dated May 11, 2018, International Searching Authority, EP.

*Primary Examiner* — Marc S Zimmer

(74) *Attorney, Agent, or Firm* — Joseph Waters; McDonald Hopkins LLC

(57) ABSTRACT

A hydrophilic silicone, compositions comprising the same, and articles comprising the same are shown and described herein. The hydrophilic silicone is an ionically modified silicone compound wherein the compound has a net neutral charge. The hydrophilic silicone compounds may be provided as part of a composition, e.g., a composition suitable for forming a hydrogel, which may be employed to form a film material and even an article (e.g., in a contact lens).

24 Claims, 3 Drawing Sheets

(56) References Cited

U.S. PATENT DOCUMENTS

| | | | |
|---|---|---|---|
| 2013/0203812 A1* | 8/2013 | Raja | A61K 47/34 514/324 |
| 2014/0088279 A1* | 3/2014 | Wolter | C08F 30/08 526/279 |
| 2015/0158889 A1* | 6/2015 | Bhat | G02B 1/043 556/418 |
| 2015/0309210 A1 | 10/2015 | Huang et al. | |
| 2017/0088564 A1* | 3/2017 | Iyer | C08F 130/02 |
| 2020/0148831 A1* | 5/2020 | Okamura | C08F 30/08 |
| 2020/0231757 A1* | 7/2020 | Dolai | C08G 77/26 |

* cited by examiner

IONICALLY MODIFIED SILICONES, COMPOSITIONS, AND MEDICAL DEVICES FORMED THEREFROM

CROSS REFERENCE TO RELATED APPLICATIONS

The present application is a 35 U.S.C. 371 national stage filing of PCT Application No. PCT/US2018/018476 filed on Feb. 16, 2018, which claims priority to and the benefit of U.S. Provisional Application No. 62/459,632 filed on Feb. 16, 2017, the entire disclosure of which are incorporated herein by reference in their entirety.

FIELD OF INVENTION

The present invention relates to silicone compounds and compositions comprising such compounds. In particular, provided are ionically modified silicone compounds having an overall charge that is net neutral, compositions comprising such silicone compounds, an active delivery system incorporating a hydrogel formed from such compositions, and articles formed from such compositions.

BACKGROUND

Contact lenses for continuous wear over a long time period are made of silicone rubber prepared from polydimethyl siloxanes. Since the silicone rubber contact lenses are very water-repellent and greatly different from the cornea in thermal properties, such as thermal conductivity and thermal diffusivity, they may give a foreign body sensation, particularly a burning sensation despite being oxygen permeable. Contact lenses made from silicone rubber tend to be uncomfortable to wear. Further, the silicone rubber is soft and elastic, making it difficult to conduct precise mechanical treatments such as cutting, grinding, and polishing. Many attempts for making the surface of silicone rubber lenses hydrophilic have been undertaken, but no completely satisfactory contact lens has been developed. High water content contact lenses are usually made of poly-N-vinylpyrrolidone polymers. Since high water content contact lenses typically contain about 60% to about 80% by weight of water, they have the disadvantages of being (a) weaker in material quality compared to low water content contact lenses, (b) easily contaminated with inorganic and organic compounds found in tears that penetrate and accumulate into the lenses during the use, and (c) bad in maintenance of lens contour due to the evaporation of water during the use, which allows the refractive power to easily change.

Reactive silicone-hydrogel formulations are used to make extended wear soft contact lenses due to their relatively high oxygen permeability, flexibility, comfort, and reduced corneal complications. Conventional hydrogel materials (e.g. 2-hydroxyethyl methacrylate, HEMA) by themselves have poor oxygen permeability and they transport oxygen to the eye through the absorbed water molecules. Water has low oxygen permeability, also called the Dk value, which may be expressed in Barrer, wherein 1 Barrer=$10^{-11}$ (cm$^3$ O$_2$) cm cm$^{-2}$ s$^{-1}$ mmHg$^{-1}$ where "cm$^3$ O$_2$" is at a quantity of oxygen at standard temperature and pressure and where "cm" represents the thickness of the material and "cm$^{-2}$" is the reciprocal of the surface area of that material. The Dk of water is about 80 Barrer. Upon exposure to atmospheric air for long periods, these lenses are slowly dehydrated and the amount of oxygen transported to the cornea is reduced. Eye irritation, redness, and other corneal complications can result, which may restrict use of the lenses to limited periods of wear. Blending reactive silicone monomers with conventional monomers is a potential solution, but such blends have been marred by compatibility issues.

A possible solution to this problem is to make the silicone monomer hydrophilic by incorporating hydrophilic units on the monomer. One approach to provide hydrophilic silicone monomers is to polymerize the organo-modified silicone monomer with organic monomers in the presence of a cross-linker. Examples of prior attempts of providing hydrophilicity include those described in U.S. Pat. Nos. 4,260,725; 5,352,714; 5,998,498; 6,867,245; 6,013,711; 6,207,782; 7,601,766; 7,557,231; 7,732,546; 7,781,558; and 7,825,273, which are each incorporated herein by reference. This approach leads to a large number of unreacted monomers due to unregulated viscosity build-up that requires extracting the leachable monomers from the matrix by water-isopropanol solvent mixtures. This leads to increased processing costs. Further, the silicone hydrogel formulations made by these methods still fail to exhibit significant wettability.

Methacryloxypropyltris-(trimethylsiloxy)silane monomers have been used to prepare silicone-containing hydrogels. The (meth)acryloxypropyltris-(trimethylsiloxy)silane is hydrophobic and is used in preparing polyurethane-silicone polymers. These polyurethane-silicone polymers contain blocks of hydrophobic silicone. Contact lenses made from these polymers may cause eye discomfort because of the hydrophobic regions within the polymer.

Silicone-hydrogels are typically made from acrylate or methacrylate functionalized silicone monomers that are polymerized with hydrophilic organic monomers, such as hydroxyethyl methacrylate (HEMA), N-vinylpyrrolidone (NVP) and other monomers such as methyl methacrylic acid (MA), and N,N-dimethylacrylamide (DMA), in the presence of crosslinkers and free radical or photoinitiators. Crosslinking agents generally have two or more reactive functional groups at different sites of the molecule. Typically, these sites contain polymerizable ethylenic unsaturation groups. During polymerization to form the silicone-hydrogel, they form a covalent bond with two different polymer chains and form a stable three-dimensional network to improve the strength of the polymer. Crosslinking agents conventionally used in contact lenses include ethylene glycol dimethacrylate and trimethyloylpropane trimethacrylate. Other useful crosslinking agents include diethyleneglycol dimethacrylate, bisphenol A dimethacrylate, diglycidyl bisphenol A dimethacrylate, and dimethacrylate-terminated polyethylene glycol, and reactive linear polyether modified silicones. The oxygen permeability of these silicone-hydrogels is affected by the chemical structure of the acrylate or methacrylate functionalized silicone monomer and choice of the other monomers containing reactive carbon-carbon double bonds that are used in preparing the cross-linked polymer.

Silicone-hydrogel contact lens materials are typically made using either hydrophobic mono-functional silicone monomers or multi-functional hydrophilic silicone monomers followed by secondary surface treatment. Mono-functional silicone monomers are often used in the contact lens industry over multi-functional silicone monomers since the latter lead to increased rigidity in the lenses made therefrom. The known mono-functional silicone monomers, however, may have deficiencies. For example, monofunctional siloxane-polyether (meth)acrylates are susceptible to air oxidation. Monofunctional (meth)acryloxy functional siloxanes that contain 1,4-substitution on the (meth)acryloxy group to the siloxane group on a six-member ring, such as for example, (meth)acrylic acid 2-hydroxy-4-[2-bis-(trimethylsiloxy)methylsilanyl-ethyl]-cyclohexyl ester, form highly ordered copolymers that may inhibit the permeability of oxygen through the silicone-hydrogel. 1,3-substitution of the (meth)acryloxy group to the siloxane group on a six-member ring, such as for example, (meth)acrylic acid 2-hydroxy-5-[2-bis-(trimethylsiloxy)methylsilanyl-ethyl]-cyclohexyl ester, form less order copolymers, but the moderate polarity of the (meth)acryloxy group may affect the hydrophilic properties of the silicone-hydrogel.

The state of this art for soft contact lenses, including the silicone-based materials described in the above mentioned patents, still possess major shortfalls like formulation compatibility, sub-optimal surface wettability, lipid deposition, the need for compatabilizers in preparing the polymer, internal wetting agents, or post processing treatments such as "plasma oxidation" surface treatments. These approaches can decrease oxygen permeability or require the use of compatabilizers, which add costs during the manufacturing process. There remains a need for hydrophilic silicone monomers with advantageous wettability and oxygen permeability that can be used to make contact lenses without the drawbacks and expensive surface treatments necessary with the native silicone containing materials of the current state of art.

Methacrylic acid containing ionic lenses provides good hydrophilicity and water content. A problem associated with methacrylic acid, however, is deposition on the lens due to anionic carboxylate groups. Deposition of tear film components on a contact lens surface causes a reduction in the overall performance of the lens and an increase in inflammatory responses. There are various factors which influence deposition on contact lens materials such as tear film composition, the ionicity of the material, water content, pore size and hydrophobicity. A large proportion of the protein in the tear film is lysozyme, and group IV materials (ionic, high water content) tend to attract this protein to a greater extent than the other groups. Group II (non-ionic, high water content) lens materials have a tendency to attract lipids from the tear film. Some SiH materials have been found to deposit considerably less protein and more lipid than conventional hydrogels, however, the pattern of deposition appears to depend on the formula of the material and whether it is surface treated. There is also the possibility that a higher percentage of denatured proteins accumulate on some SiH lenses as the protein is not able to penetrate the matrix of the lens due to surface treatment.

Treatment of ocular diseases, conventionally utilizes topical administration to achieve therapeutic drug concentration within the eye. Topical therapy mainly includes instillation of drops, ointments or lotions into the eye. However, significant drug losses occur upon administration of eye drops due to dilution and washing of the drug by reflex tearing and blinking or draining through the nasolacrimal system, which limit its therapeutic efficiency. Wherein, use of ointment or lotion have longer contact time with the cornea and provides more drug absorption but distorts and blurs the patient's vision.

With a need to enhance the drug residence time and its absorption for enhanced bioavailability, use of contact lens for ocular delivery was introduced. Examples of prior attempts on ocular drug delivery include those described in U.S. Pat. Nos. 8,414,912; 9,102,105; 8,349,351; 8,404,271 and EP 2370054, which are each incorporated herein by reference. A number of researchers in the past have used contact lenses upon soaking in the drug solution followed by insertion (European Journal of Clinical pharmacology, 1999, 55(4): 317-323). U.S. Pat. No. 8,273,366 discloses a drug delivery system, comprising a contact lens having dispersed nanoparticles of an ophthalmic drug. Moreover, U.S. Pat. No. 7,638,137 and EP 2 543 358 B1 describe a method for effective ocular delivery using nanocarrier or drug encapsulant approach in P-HEMA (poly-2-hydroxy ethyl-methacrylate) or PMAA (poly(methacrylate acid)) containing hydrogel contact lenses. An article in Int. J. Pharm. (2003, vol. 257, no. 1-2, pages 141-151) describes the in vitro uptake and release behavior of tromolyn sodium, ketotifen-fumarate, ketorolac tromethamine and dexamethasone sodium phosphate with silicone- and p-HEMA-containing hydrogel contact lenses.

While the uptake and release of drugs from silicone contact lenses has been explored, there remains a need for controlled and sustained release of medication to the eye using contact lens as a device. Incorporation of functional monomers in the hydrogel upon interaction with the drugs enhance their uptake as well as allows its sustainable release.

Hence, there remains a need for hydrophilic silicone monomers with advantageous wettability, stability to air oxidation, high oxygen permeability, low debris formation, and high solubility in the other reactive monomers used to make the polymer without the need for compatibilizers.

SUMMARY

The following presents a summary of this disclosure to provide a basic understanding of some aspects. This summary is intended to neither identify key or critical elements nor define any limitations of embodiments or claims. Furthermore, this summary may provide a simplified overview of some aspects that may be described in greater detail in other portions of this disclosure.

The present invention relates to a silicone compound (e.g., monomer, macromer, polymer and its hydrogel formulations) and a drug delivery system comprising such silicone compounds. In aspects, the present invention provides ionically modified silicones having an overall charge that is net neutral. Drug delivery systems comprising hydrogels derived from such ionically modified silicones are useful in providing the benefits of wettability, formulation compatibility, stability to air oxidation, gas permeability, and provide less debris formation. They may, in aspects hereof, also impart antimicrobial properties to the compositions and materials (e.g., contact lenses) formed from such materials. They can be also utilized to retain or release active substances, such as pharmaceutically active substances, through ionic-ionic interactions.

In one aspect, provided is a silicone compound of the Formula (I):

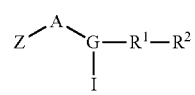

(I)

where $R^1$ is chosen from a chemical bond or a divalent group comprising 1 to 16 carbon atoms optionally containing a heteroatom chosen from oxygen, sulfur, or nitrogen;

$R^2$ is a linear, branched, cyclic, or cage like siloxanyl moiety, or a silane moiety having the general structure (a)

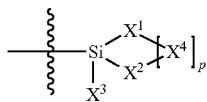

$X^1$ is independently selected from linear or branched alkyl group containing 1-16 carbon atoms, trimethoxy silyl, trimethylsilyloxy, —O[Si(CH$_3$)$_2$O—]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si(CH$_3$)$_2$O—, or (CH$_3$)$_3$Si(CH$_2$CH$_2$Si(CH$_3$)$_2$O)$_s$— wherein s is an integer chosen from 0-200;

$X^2$ is independently selected from a linear or branched alkyl group containing 1-16 carbon atoms, trimethoxy silyl, trimethylsilyloxy, —O[Si(CH$_3$)$_2$O—]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si(CH$_3$)$_2$O—, or (CH$_3$)$_3$Si(CH$_2$CH$_2$Si(CH$_3$)$_2$O)$_z$— wherein z is an integer chosen from 0-200, or —[OSi(CH$_3$)$_2$]$_m$G$^1$, wherein G$^1$ is (CH$_3$)$_3$SiO— and m is an integer from 0 to 400, or a reactive or non-reactive silicone group with the general Formula (b1) or (b2):

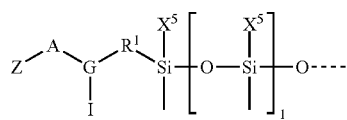

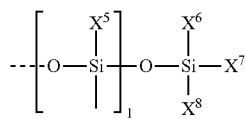

where l is an integer chosen from 0-200; and p in Formula (a) is 0 when $X^2$ is of the Formula (b1) or (b2);

$X^3$ and $X^5$ are independently chosen from a C1-C6 alkyl, trimethylsiloxy, (CH$_3$)$_3$SiCH$_2$CH$_2$—, (CH$_3$)$_3$SiCH$_2$CH$_2$Si(CH$_3$)$_2$O—, and —OSi(CH$_3$)$_2$, with the provisos that (i) when $X^1$ or $X^6$ is —O[Si(CH$_3$)$_2$O—]$_n$, then $X^3$ and $X^5$, respectively, is —OSi(CH$_3$)$_2$ and $X^1$ forms a chemical bond with the $X^3$ and $X^5$ forms a chemical bond with $X^6$ to correspondingly form a divalent —$X^1$—$X^3$— or $X^5$—$X^6$— group, which is bonded to the silicon atom to form a cyclic polysiloxane ring, and (ii) when $X^3$ and/or $X^5$ is —OSi(CH$_3$)$_2$, then $X^1$ and/or $X^6$ is —O[Si(CH$_3$)$_2$O—]$_n$, and $X^1$ forms a chemical bond with the $X^3$ and/or $X^5$ forms a chemical bond with $X^6$ to form a divalent —$X^1$—$X^3$— or $X^5$—$X^6$— group, which is bonded to the silicon atom to form a cyclic polysiloxane ring;

where, $X^1$, $X^2$ and $X^3$ optionally can each be —O[Si(CH$_3$)$_2$O—]$_n$, and interconnected to form a polysilsesquioxane ring as described in formula (b3) and R$^7$ is independently chosen from a linear or branched alkyl or aralkyl group;

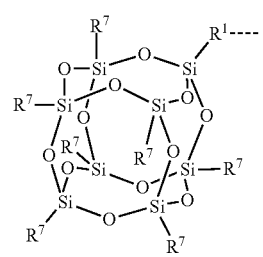

$X^6$, $X^7$, and $X^8$ are independently chosen from a linear or branched alkyl group containing 1-16 carbon atoms, alkoxy, trimethylsilyloxy, or —O[Si(CH$_3$)$_2$O—]$_n$, wherein n is an integer chosen from 1 to 9, and wherein $X^6$ and $X^7$, $X^7$ and $X^8$, or $X^6$ and $X^8$ may form a ring;

$X^4$ is an optional connecting group selected independently from dimethylsiloxy, —O[Si(CH$_3$)$_2$O—], or —CH$_2$CH$_2$(CH$_3$)$_2$SiO-moiety;

p is an integer chosen from 0-10;

G is a bridging unit between the siloxane moiety and reactive moiety independently selected from a linear or branched alkyl group or a carbocyclic group optionally contains hetero atoms;

A is a heteroatom;

I is an ionic containing moiety with 0-200 carbon atoms optionally containing heteroatoms, where the ionic containing moiety is counterbalanced with a counterion; and Z is a polymerizable group having the general Formula (c):

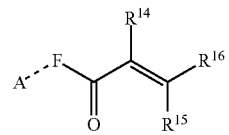

wherein R$^{14}$, R$^{15}$, and R$^{16}$ are independently chosen from hydrogen or monovalent hydrocarbon radical with 1-5 carbon atoms; and F is a linker group chosen from aliphatic, cycloaliphatic, or aromatic hydrocarbon radical having 1-16 carbon atoms and optionally containing a heteroatom.

In one embodiment, I is of the formula:

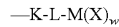

wherein K is a divalent hetero atom, and in one embodiment K is an oxygen atom,

L is a chemical bond or a divalent hydrocarbon radical comprising a substituted or unsubstituted, linear or branched, aliphatic or aromatic hydrocarbon with 1-50 carbon atoms, which may optionally contain heteroatoms, and in embodiments can comprise functionalities independently chosen from an alcohol, an ether, an ester, an amide, an amine, a urea, a urethane, a cyano, a carbonate, a carbamate, a thiol, a thioether, a thiol ester, or a combination of two or more thereof;

M and X are an ionic functional group or ionic functional group forming compound, wherein M and X are oppositely charged species which are not chemically bonded to each other;

and w is 1 to 10.

In one embodiment, M is independently chosen from:

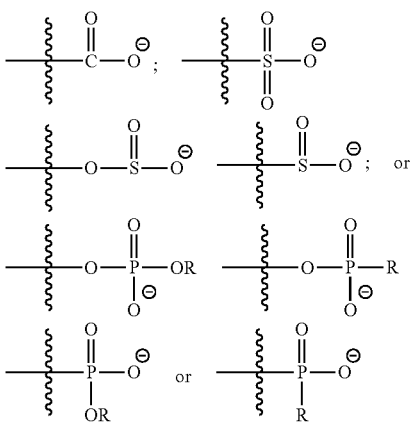

X is independently chosen from a quaternary ammonium compound, a quaternary ammonium group forming compound, a cationic polymer, a group 15 elements chosen from N, P, As, Sb, or Bi, a metal, an alkali metal, an alkaline earth metal, a transition metals, a rare-earth metal or a combination thereof.

In one embodiment, X is independently chosen from:

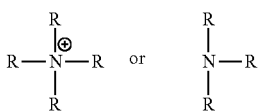

where R is independently selected from hydrogen, an alkyl, an aryl, an aralkyl, and a cycloaliphatic with 1-100 carbon atoms with optional heteroatoms which may contain functional groups like hydroxy, amide, urethane, urea, ester, amine, thiol, disulfide, ether, and the formula

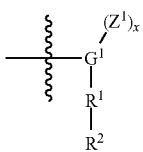 (i)

wherein $G^1$ is an alkyl, an aryl, an aralkyl, and a cycloaliphatic with 1-100 carbon atoms with optional heteroatoms; $Z^1$ is a reactive or non-reactive functional moiety of formula

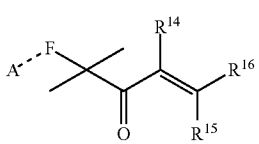 (C1)

wherein $R^{14}$, $R^{15}$, and $R^{16}$ are independently chosen from hydrogen or monovalent hydrocarbon radical with 1-5 carbon atoms; and F is a linker group chosen from aliphatic, cycloaliphatic, or aromatic hydrocarbon radical having 1-16 carbon atoms and optionally containing a heteroatom; and A is chosen from none or a heteroatom; and R1 and R2 are as defined in claim 1 and x is 0-10.

In one embodiment of the compound of any previous embodiment, wherein X is a cationic polymer chosen from, a poly(ethylene amine), a poly(pyridine), a poly(immidazolium), a poly-acrylate based quaternary ammonium salt, or a combination of two or more thereof.

In one embodiment of the compound of any previous embodiment, K is oxygen, L is a C1-C6 divalent hydrocarbon radical, and M is —C(O)—OH.

In an other aspect, provided is a composition comprising (A) a hydrogel material and (B) an active substance, wherein the hydrogel material (A) is formed from a reaction mixture comprising the silicone compound of any previous embodiment.

In one embodiment, the reaction mixture from which the hydrogel material (A) is formed comprises the organic monomer, which chosen from a vinylic monomer, an acrylamide monomer, an acrylic monomer, or a combination of two or more thereof.

In one embodiment of the composition of any previous embodiment, (a) the vinylic monomer is chosen from N-vinyl-pyrrolidone, N-vinyl-caprolactam, N-vinyl-acetamide, N-vinyl-formamide, N-vinyl-isopropylamide, vinyl benzene, vinyl naphthalene, vinyl pyridine, vinyl alcohol, vinyl containing silicone, or a combination of two or more thereof; (b) the acrylic monomer is chosen from 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-dimethylacrylamide, N-isopropylacrylamide, acrylamide, methacrylamide, acrylic acid, methacrylic acid, acrylated hydrophilic or hydrophobic organo-silicone, or a combination of two or more thereof.

In one embodiment of the composition of any previous embodiment, the reaction mixture from which the hydrogel material (A) is formed further comprises (i) optionally an active ingredient that is reactive or non-reactive to actinic curing conditions; and (ii) optionally, an organic monomer, an organic macromer, a reactive polymer, a cross-linker, a compatibilizer, a tinting agent, an initiator, or a combination of two or more thereof.

In one embodiment of the composition of any previous embodiment, the silicone compound of Formula (I) is present in an amount of from about 5 weight percent to about 90 weight percent of the composition.

In one embodiment of the composition of any previous embodiment, the ratio of the silicone compound of Formula (I) to organic monomer is about 1:99 to 99:1.

In one embodiment of the composition of any previous embodiment, the active substance (B) is chosen from an agent affecting the central nervous system, an antiallergic agent, a cardiovascular agent, an agent affecting respiratory organs, an agents affecting digestive organ, hormone preparations, an agent affecting metabolism, an antitumor agent, an antibiotic preparation, a chemotherapeutic, an antimicrobial, a local anesthetic, an antihistaminic, antiphlogistic, an astringent, a vitamin, an antifungal agent, a peripheral nervous anesthetic, a vasodilator, a crude drug essence, a tincture, a crude drug powder, a hypotensive agent, an immunosuppressant, a lubricating agent, a wetting agent or a combination of two or more thereof.

In one embodiment of the composition of any previous embodiment, the active substance (B) is an ophthalmically active drug.

In one embodiment of the composition of any previous embodiment, the ophthalmically active drug is chosen from pilocarpine, epinephrine, tetracycline, phenylephrine, eserine, phospholine iodide, demecarium bromide, cyclopentolate, homatropine, scopolamine, chlortetracycline, bacitracin, neomycin, polymixin, gramicidin, oxytetracycline, chloramphenicol, gentamycin, penicillin, erythromycin, carbachol, sulfacetamide, polymixin B, idoxuridine, isoflorophate, fluoromethalone, dexamethasone, hydrocortisone, hydrocortisone acetate, dexamethasone 21-phosphate, fluorocinolone, medrysone, prednisolone, methyl prednisolone, prednisolone 21-phosphate, prednisolone acetate, betamethasone, Ibuprofen, Flurbiprofen, Cloricromene, Diclofenac diethyl ammonium, Piroxicam, Methylprednisolonem, triamcinolone, timolol maleate, ketotifen fumarate, moxifloxacin hydrochloride monohydrate or a combination of two or more thereof.

In still another aspect, provided is a gel formed from the composition of any previous embodiment.

In one embodiment, the gel is in the form of a film.

In still yet another aspect, provided is a hydrogel formed from the composition of any previous embodiment.

In one embodiment, the hydrogel comprises an active ingredient.

In one embodiment, the hydrogel of any previous embodiment is in the form of a contact lens.

In one embodiment, provided is a contact lens made of the hydrogel according to any previous embodiment.

In still yet a further aspect, provided is an actives delivery system comprising the composition, gel, or hydrogel according to any previous embodiment.

In one embodiment of the actives delivery system, the reaction mixture from which the hydrogel material is formed further comprises (i) optionally an active ingredient that is reactive or non-reactive to actinic curing conditions; and (ii) optionally, an organic monomer, an organic macromer, a reactive polymer, a cross-linker, a compatibilizer, a tinting agent, an initiator, or a combination of two or more thereof.

In one embodiment of the actives delivery system according to any previous embodiment, the reaction mixture from which the hydrogel material is formed comprises the organic monomer, which chosen from a vinylic monomer, an acrylamide monomer, an acrylic monomer, or a combination of two or more thereof.

In one embodiment of the actives delivery system according to any previous embodiment, (a) the vinylic monomer is chosen from N-vinyl-pyrrolidone, N-vinyl-caprolactam, N-vinyl-acetamide, N-vinyl-formamide, N-vinyl-isopropylamide, vinyl benzene, vinyl naphthalene, vinyl pyridine, vinyl alcohol, vinyl containing silicone, or a combination of two or more thereof; (b) the acrylic monomer is chosen from 2-hydroxy-ethyl-methacrylate (HEMA), 2-hydroxy-ethyl-acrylate (HEA), hydroxyl propyl methacrylate, trimethyl-ammonium 2-hydroxy propyl methacrylate hydrochloride, dimethylaminoethyl methacrylate, glycerol methacrylate, N,N-dimethylacrylamide, N-isopropylacrylamide, acrylamide, methacrylamide, acrylic acid, methacrylic acid, acrylated hydrophilic or hydrophobic organo-silicone, or a combination of two or more thereof.

In one embodiment of the actives delivery system according to any previous embodiment, the silicone compound of Formula (I) is present in an amount of from about 1 weight percent to about 99 weight percent of the composition.

In one embodiment of the actives delivery system according to any previous embodiment, the ratio of the silicone compound of Formula (I) to organic monomer is about 1:99 to 99:1.

In one embodiment of the actives delivery system according to any previous embodiment, the pharmaceutically active substance is chosen from an agent affecting the central nervous system, an antiallergic agent, a cardiovascular agent, an agent affecting respiratory organs, an agents affecting digestive organ, hormone preparations, an agent affecting metabolism, an antitumor agent, an antibiotic prepartion, a chemotherapeutic, an antimicrobial, a local anesthetic, an antihistaminic, antiphlogistic, an astringent, a vitamin, an antifungal agent, a peripheral nervous anesthetic, a vasodilator, a crude drug essence, a tincture, a crude drug powder, a hypotensive agent, an immunosuppressant, or a combination of two or more thereof.

In one embodiment of the actives delivery system according to any previous embodiment, the pharmaceutically active substance is an ophthalmically active drug.

In one embodiment of the actives delivery system according to any previous embodiment, the ophthalmically active drug is chosen from pilocarpine, epinephrine, tetracycline, phenylephrine, eserine, phospholine iodide, demecarium bromide, cyclopentolate, homatropine, scopolamine, chlortetracycline, bacitracin, neomycin, polymixin, gramicidin, oxytetracycline, chloramphenicol, gentamycin, penicillin, erythromycin, carbachol, sulfacetamide, polymixin B, idoxuridine, isoflorophate, fluoromethalone, dexamethasone, hydrocortisone, hydrocortisone acetate, dexamethasone 21-phosphate, fluorocinolone, medrysone, prednisolone, methyl prednisolone, prednisolone 21-phosphate, prednisolone acetate, betamethasone, Ibuprofen, Flurbiprofen, Cloricromene, Diclofenac diethyl ammonium, Piroxicam, Methylprednisolonem, triamcinolone, or a combination of two or more thereof.

In one embodiment of the actives delivery system according to any previous embodiment, the hydrogel material is a hydrogel film.

In one embodiment of the actives delivery system according to any previous embodiment, the hydrogel material is in the form of a contact lens.

In one embodiment, provided is a contact lens made of the hydrogel according to any previous embodiment.

In one embodiment, provided is a contact lens made of the actives delivery system according to any previous embodiment.

In still yet another aspect, provided is a medical device comprising the actives delivery system of any previous embodiment.

In one embodiment, the device is chosen from a probe, a wand, a film, a band, a patch, a contact lens, or an insert.

The following description and the drawings disclose various illustrative aspects. Some improvements and novel aspects may be expressly identified, while others may be apparent from the description and drawings.

BRIEF DESCRIPTION OF THE DRAWINGS

Various embodiments are described below with reference to the drawings wherein.

DETAILED DESCRIPTION

Figure 1:
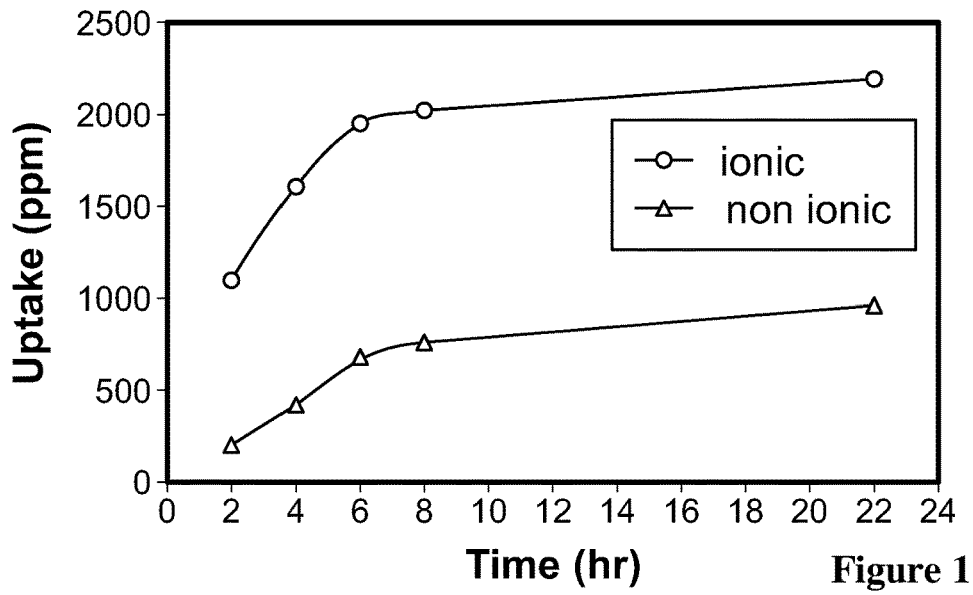
FIG. 1. is a graph illustrating the uptake of Timolol maleate with time.

Reference will now be made to exemplary embodiments, examples of which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments. In this disclosure, numerous specific details provide a thorough understanding of the subject disclosure. It should be understood that aspects of this disclosure may be practiced with other embodiments not necessarily including all aspects described herein, etc.

As used herein, the words "example" and "exemplary" means an instance, or illustration. The words "example" or "exemplary" do not indicate a key or preferred aspect or embodiment. The word "or" is intended to be inclusive rather than exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

The present invention relates to a silicone compound, such as a monomer, macromere, or polymer compositions comprising such compounds and articles formed from such compositions. The composition may be used to form a hydrogel. The composition may be contact lens forming compositions comprising ionically modified silicones, vinylic monomers, active ingredients, and cross-linkers. The ionically modified silicone hydrogel contact lenses are useful in providing the benefits of wettability, formulation compatibility, stability to air oxidation, gas permeability, and provide less debris formation when net charge is neutral. They can be also utilized to retain or release the active substances through ionic-ionic interactions and be provided as part of a drug delivery system.

A "macromer" refers to a medium to high molecular weight compound or polymer that contains functional groups capable of undergoing further polymerizing/crosslinking reactions. Medium and high molecular weight typically means average molecular weights greater than 700 Daltons. Preferably, a macromer contains ethylenically unsaturated groups and can be polymerized actinically or thermally.

"Molecular weight" of a polymeric material (including monomeric or macromeric materials), as used herein, refers to the number-average molecular weight unless otherwise specifically noted or unless testing conditions indicate otherwise.

A "polymer" means a material formed by polymerizing/crosslinking one or more monomers, macromers and or oligomers.

A "vinylic monomer", as used herein, refers to a low molecular weight compound that has an ethylenically unsaturated group and can be polymerized actinically or thermally. Low molecular weight typically means average molecular weights less than 700 Daltons.

A "hydrophilic vinylic monomer", as used herein, refers to a vinylic monomer which is capable of forming a homopolymer that can absorb at least 10 percent by weight water when fully hydrated.

A "hydrophobic vinylic monomer", as used herein, refers to a vinylic monomer which is capable of forming a homopolymer that can absorb less than 10 percent by weight water when fully hydrated.

"A binder polymer" refers to a crosslinkable polymer that can be crosslinked by a crosslinker or upon initiation by a chemical or physical means (e.g., moisture, heating, UV irradiation or the like) to trap or bind colorants onto or into a medical device (preferably a contact lens) such as that term is known in the art.

A "photoinitiator" refers to a chemical that initiates radical crosslinking and/or polymerizing reaction by the use of light.

A "thermal initiator" refers to a chemical that initiates radical crosslinking/polymerizing reaction by the use of heat energy.

A "cage like" siloxane or siloxanyl structure refers to polysesquioxane type structure.

An "active" refers to an ingredient or a chemical that can be delivered from a medical device.

In one aspect, provided is a silicone compound. The silicone compound is configured such that is hydrophilic. In accordance with the present compounds, the silicone compound is an ionically modified compound having a net neutral charge. The silicone compounds are ionically modified with an ionic group, ionic forming group, and the compound is provided such that it has an overall net neutral charge. Providing a silicone compound with these groups has been found to provide a hydrophilic compound. The compounds are water dispersible and may undergo polymerization to provide a hydrophilic material.

Provided is a silicone compound of the Formula (I):

(I)

where $R^1$ is chosen from a chemical bond or a divalent group comprising 1 to 16 carbon atoms and optionally a heteroatom chosen from oxygen, sulfur, or nitrogen; $R^2$ is a linear, branched, cyclic, or cage like siloxanyl moiety, or a silane moiety having the general structure (a)

(a)

$X^1$ is independently selected from linear or branched alkyl group containing 1-16 carbon atoms, trimethoxy silyl, trimethylsilyloxy, —O[Si(CH$_3$)$_2$O—]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si(CH$_3$)$_2$O—, or (CH$_3$)$_3$Si(CH$_2$CH$_2$Si(CH$_3$)$_2$O)$_s$— wherein s is an integer chosen from 0-200;

$X^2$ is independently selected from a linear or branched alkyl group containing 1-16 carbon atoms, trimethoxy silyl, trimethylsilyloxy, —O[Si(CH$_3$)$_2$O—]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si(CH$_3$)$_2$O—, or (CH$_3$)$_3$Si(CH$_2$CH$_2$Si(CH$_3$)$_2$O)$_z$— wherein z is an integer chosen from 0-200, or —[OSi(CH$_3$)$_2$]$_m$G$^1$, wherein G$^1$ is (CH$_3$)$_3$SiO— and m is an integer from 0 to 400, or a reactive or non-reactive silicone group with the general Formula (b1) or (b2):

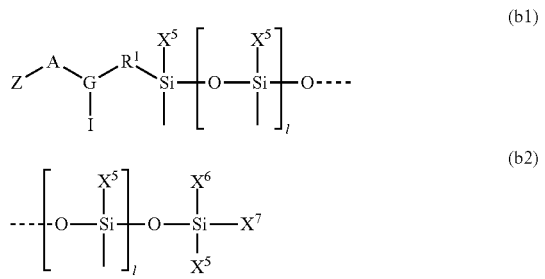

where l is an integer chosen from 0-200; and p in Formula (a) is 0 when $X^2$ is of the Formula (b1) or (b2);

$X^3$ and $X^5$ are independently chosen from a C1-C6 alkyl, trimethylsiloxy, (CH$_3$)$_3$SiCH$_2$CH$_2$—, (CH$_3$)$_3$SiCH$_2$CH$_2$Si(CH$_3$)$_2$O—, and —OSi(CH$_3$)$_2$, with the provisos that (i) when $X^1$ or $X^6$ is —O[Si(CH$_3$)$_2$O—]$_n$, then $X^3$ and $X^5$, respectively, is —OSi(CH$_3$)$_2$ and $X^1$ forms a chemical bond with the $X^3$ and $X^5$ forms a chemical bond with $X^6$ to correspondingly form a divalent —X$^1$—X$^3$— or X$^5$—X$^6$— group, which is bonded to the silicon atom to form a cyclic polysiloxane ring, and (ii) when $X^3$ and/or $X^5$ is —OSi(CH$_3$)$_2$, then $X^1$ and/or $X^6$ is —O[Si(CH$_3$)$_2$O—]$_n$, and $X^1$ forms a chemical bond with the $X^3$ and/or $X^5$ forms a chemical bond with $X^6$ to form a divalent —X$^1$—X$^3$— or X$^5$—X$^6$— group, which is bonded to the silicon atom to form a cyclic polysiloxane ring;

where, $X^1$, $X^2$ and $X^3$ optionally can each be —O[Si(R$^7$)O—]$_n$, and interconnected to form a polysilsesquioxane ring as described in formula (b3) and R$^7$ is independently chosen from a linear or branched alkyl or aralkyl group;

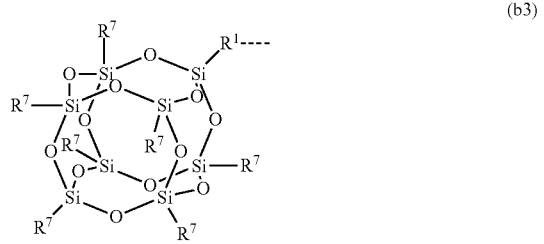

$X^6$, $X^7$, and $X^8$ are independently chosen from a linear or branched alkyl group containing 1-16 carbon atoms, alkoxy, trimethylsilyloxy, or —O[Si(CH$_3$)$_2$O—]$_n$, wherein n is an integer chosen from 1 to 9, and wherein $X^6$ and $X^7$, $X^7$ and $X^8$, or $X^6$ and $X^8$ may form a ring;

$X^4$ is an optional connecting group selected independently from dimethylsiloxy, —O[Si(CH$_3$)$_2$O—]$_n$, or —CH$_2$CH$_2$(CH$_3$)$_2$SiO-moiety;

p is an integer chosen from 0-10;

G is a bridging unit between the siloxane moiety and reactive moiety independently selected from a linear or branched alkyl group or a carbocyclic group optionally contains hetero atoms;

A is a heteroatom, and in one embodiment is chosen between oxygen or sulfur;

I is an ionic containing moiety with 0-200 carbon atoms optionally containing heteroatoms, where I is counter-balanced with a counter ion to provide a net neutral charge; and Z is a polymerizable group having the general Formula (c):

wherein R$^{14}$, R$^{15}$, and R$^{16}$ are independently chosen from hydrogen or monovalent hydrocarbon radical with 1-5 carbon atoms; and F is a linker group chosen from aliphatic, cycloaliphatic, or aromatic hydrocarbon radical having 1-16 carbon atoms and optionally containing a heteroatom.

In embodiments, R$^1$ may be chosen from a divalent C1-C16 alkyl group that optionally contains a heteroatom chosen from oxygen, sulfur, or nitrogen. In one embodiment, R$^1$ is chosen from a bond or a divalent C1-C16 alkyl, a divalent C2-C10 alkyl, even a divalent C4-C6 alkyl group. In R', the divalent alkyl group refers to the number of carbon atoms in the divalent alkyl chain. The divalent alkyl groups for R$^1$ may be CH$_2$ groups or carbon groups in which the hydrogen atoms may be substituted with other groups chosen from a C1-C10, C2-C8, or C4-C6 linear, branched, or cyclic hydrocarbon radical that optionally contains heteroatoms. In one embodiment, R$^1$ is chosen from a divalent radical of the formula:

wherein R$^4$, R$^5$ and R$^6$ are independently chosen from hydrogen, a linear, branched, or cyclic hydrocarbon radical with 1 to 10 carbon atoms, 1 to 6 carbon atoms, 1 to 4 carbon atoms, or 1-2 carbon atoms optionally containing heteroatoms, R$^3$ is a hydrocarbon radical with 1 to 5 carbon atoms, 1 to 4 carbon atoms, or 1 to 2 carbon atoms; and q is an integer chosen from 0 to 10. In one embodiment, R$^4$-R$^6$ are chosen from hydrogen or a C1-C5 hydrocarbon. In one embodiment, R$^3$-R$^6$ are each chosen from a C1-C6 hydrocarbon radical. In one embodiment, R$^3$-R$^6$ are each methyl.

Regarding $R^2$, it will be appreciated that $X^1$ and $X^2$ are divalent groups if p is greater than 0, and monovalent groups if p is 0.

In one embodiment, the G group is chosen from a divalent linear or branched alkyl group, or a divalent carbocyclic group. In one embodiment, G is a branched alkyl moiety with the general formula:

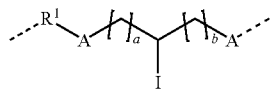
(e)

wherein a is 0-16 and b is 1.

In one embodiment, G comprises a saturated carbocyclic unit comprising 5 to 10 carbon atoms with the general formula

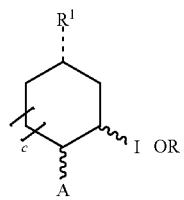
(f1)

(f2)

and isomers thereof, where c is 0-5.

In one embodiment, c is 1, and G is a cyclohexylene group. The A and R groups can be attached to the G group such that the A and R groups are oriented para or meta to one another. In one embodiment, the G unit is a cyclohexylene group and arranged in the compound as follows:

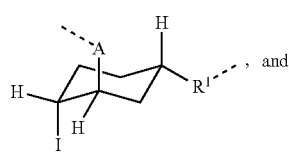
(f3)

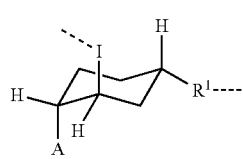
(f4)

In one embodiment G is a chosen from one or more of the following conformers:

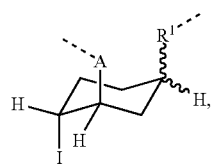
(f5)

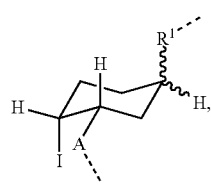
(f6)

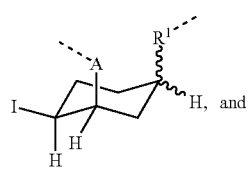
(f7)

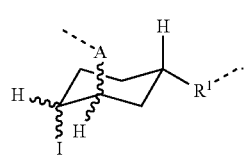
(f8)

The I group is individually chosen from an ionic moiety and an ionic forming moiety. The I group is provided such that the silicone compound has a net neutral charge. In one embodiment, the ionic moiety comprises an anionic moiety and a cationic moiety. In one embodiment, the ionic forming moiety comprises an anionic forming moiety and a cationic forming moiety.

In one embodiment, the I group is chosen from a group of the formula:

$$K\text{-}L\text{-}M(X)_w \quad (g)$$

wherein K is a divalent hetero atom, and in one embodiment K is an oxygen atom,

L is a chemical bond or a divalent hydrocarbon radical comprising a substituted or unsubstituted, linear or branched, aliphatic or aromatic hydrocarbon with 1-50 carbon atom, which may optionally contain heteroatoms, and in embodiments can comprise functionalities independently chosen from an alcohol, an ether, an ester, an amide, an amine, a urea, a urethane, a cyano, a carbonate, a carbamate, a thiol, a thioether, a thiol ester, or a combination of two or more thereof;

M and X are ionic functional group or an ionic functional group forming compound, wherein M and X are oppositely charged species that are not chemically bonded to each other and w is 1 to 10. Examples of suitable anionic or anion forming functional groups for M include, but are not limited to, the groups:

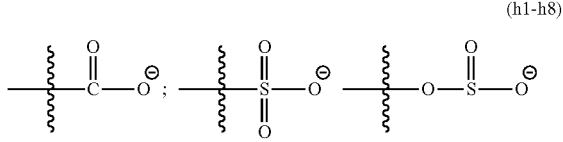
(h1-h8)

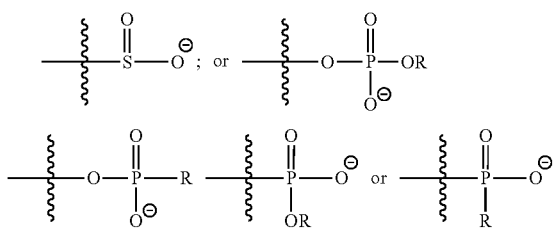

where R is independently selected from hydrogen, alkyl, an aryl, an aralkyl, and a cycloaliphatic with 1-100 carbon atoms with optional heteroatoms which may contain functional groups like hydroxy, amide, urethane, urea, ester, amine, thiol, disulfide, ether, and the formula

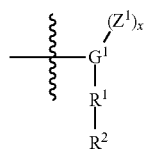
(i)

wherein $G^1$ is an alkyl, an aryl, an aralkyl, and a cycloaliphatic with 1-100 carbon atoms with optional heteroatoms. Examples of suitable cationic or cation forming functional groups X include, but are not limited to, a quaternary ammonium compound, a quaternary ammonium forming compound, a cationic polymer, a group 15 elements (e.g., N, P, As, Sb, Bi), metals, alkali metals, alkaline earth metals, transition metals, rare-earth metals or a combination thereof. Examples of suitable quaternary ammonium compounds include, but are not limited to, alkyl, aralkyl, cycloaliphatic, aromatic, branched or unbranched amines. Examples of suitable cationic polymers include, but are not limited to, poly(ethylene amine), poly(pyridines), poly(immidazoliums), poly-acrylate based quaternary ammonium salts e.g. poly(2-trimethyl ammonium ethyl acrylate), poly(2-aminoethyl acrylate). In embodiments, the cationic groups may be of the formula (h1), (h2):

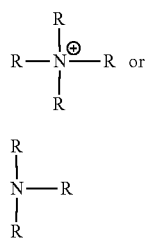

where R is independently selected from hydrogen, alkyl, an aryl, an aralkyl, and a cycloaliphatic with 1-100 carbon atoms with optional heteroatoms which may contain functional groups like hydroxy, amide, urethane, urea, ester, amine, thiol, disulfide, ether, and the formula

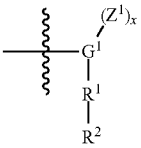
(i)

wherein $G^1$ is an alkyl, an aryl, an aralkyl, and a cycloaliphatic with 1-100 carbon atoms with optional heteroatoms;

$Z^1$ is a reactive or non reactive functional moiety of formula

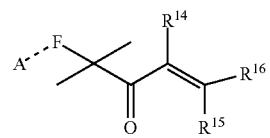
(C1)

wherein $R^{14}$, $R^{15}$, and $R^{16}$ are independently chosen from hydrogen or monovalent hydrocarbon radical with 1-5 carbon atoms; and F is a linker group chosen from aliphatic, cycloaliphatic, or aromatic hydrocarbon radical having 1-16 carbon atoms and optionally containing a heteroatom; and A is chosen from none or a heteroatom; and R1 and R2 are as defined in claim 1 and x is 0-10.

In one embodiment, X is independently selected from the following structure:

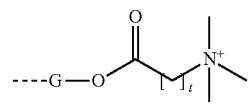

where t is 1-16.

In embodiments, w is 1-10; 1-5; even 1-2. While not wishing to be bound by any particular theory, M and X are connected by an ionic bond or ionic interaction. M and X bonding is made by reacting anionic and cationic structures with available counter ions.

When L is a group that does not contain any carbon atoms then K is directly bonded to the M group. When L is a chemical bond then the M group cannot contain —NR$_2$, —OPO(OR)$_2$, —OSO$_3$H, or —OH groups.

In one embodiment, L is chosen from a C1-C10 divalent hydrocarbon radical, which may be linear or branched. The divalent hydrocarbon radical L may be saturated or contain unsaturated bonds. In one embodiment, L is chosen from a C1-C8 divalent hydrocarbon radical, a C1-C6 divalent hydrocarbon radical; even a C1-C4 divalent hydrocarbon radical. In one embodiment, L is chosen from a C4 saturated divalent hydrocarbon radical or a C4 divalent hydrocarbon radical containing at least one unsaturated bond.

F is a linker group chosen from aliphatic, cycloaliphatic, or aromatic hydrocarbon radical having 1-16 carbon atoms and optionally containing a heteroatom. Optionally F is a bond such that the A group is directly linked to the carbonyl group in Formula (l). In one embodiment, F has the general formula (m):

 (I)

wherein n is an integer selected from 0 to about 15; S is a divalent heteroatom independently selected from O, $CH_2$, $NR^{19}$, or sulfur; J is independently selected from functional groups —C(O)—, —$NR^{20}$C(O)—, —OC(O)—, —OS(O)—, or —P(O)$OR^{21}$; $R^{17}$ and $R^{18}$ are independently chosen from a hydrocarbon radical with 1 to 5 carbon atoms; $R^{19}$, $R^{20}$ and $R^{21}$ are independently selected from hydrogen or a monovalent hydrocarbon radical with 1-5 carbon atoms. In one embodiment F has the following general structure (18):

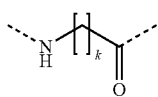 (m)

wherein k is 0-5.

Also provided is a curable composition comprising (a) a silicone compound of Formula I; (b) an active ingredient that is reactive or non-reactive to actinic curing conditions; and (c) optionally, an organic monomer, an organic macromer, a reactive polymer, a cross-linker, a compatibilizer, a tinting agent, an initiator, or a combination of two or more thereof.

The silicone compounds may be used to form a gel material. A "gel" is a colloidal system having solid character in which the colloidal constituents form a continuous (interpenetrating) network in a dispersing medium whose kinetics are slower than those of the colloidal constituents. The dispersed constituents are held together by covalent bonds, hydrogen bonds, dipole forces, van der Waals forces and/or by mechanical intertwining. Gels may be subdivided into different categories based on their dispersing medium (water, alcohol, organic solvents, air) including hydrogels (for water), alkogels (for alcohol), lyogels (for organic solvents) and aerogels (for air). If air is contained as a dispersant, gels are additionally differentiated according to the type of drying/preparation. If the gel liquid was removed by simple drying, forming a liquid/vapor interface, the dried gel is termed a "xerogel". If the gel liquid was removed above its critical point and pressure (supercritical conditions), the dried gel is termed an "aerogel". Because of the supercritical conditions, no interface is formed. If the liquid was removed by freeze drying, the dried product is termed a "cryogel". Here, the solid/gas interface is overcome by sublimation.

The organic monomer may be chosen from olefinically unsaturated group containing compounds containing at least one —C═C— group, such as, without limitation, acryloyl, methacryloyl, allyl, vinyl, styrenyl, acrylic or other —C═C— containing groups. Exemplary acrylic monomer without limitation comprises of 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-dimethylacrylamide, N-isopropylacrylamide, acrylamide, methacrylamide, acrylic acid, methacrylic acid, acrylated hydrophilic or hydrophobic organo-silicone, or a combination of two or more thereof.

The organic monomer may be chosen from a vinylic monomer such as N-vinyl-pyrrolidone, N-vinyl-caprolactam, N-vinyl-acetamide, N-vinyl-formamide, N-vinyl-isopropylamide, vinyl benzene, vinyl naphthalene, vinyl pyridine, vinyl alcohol, vinyl containing silicone, or a combination of two or more thereof.

Examples of vinyl containing silicone include siloxane-containing vinylic monomers such as, without limitation, methacryloxyalkylsiloxanes, 3-methacryloxy propylpentamethyldisiloxane, bis(methacryloxypropyl)tetramethyldisiloxane, monomethacrylated polydimethylsiloxane, mercapto-terminated polydimethylsiloxane, N-[tris(trimethylsiloxy)silylpropyl]acrylamide, N-[tris(trimethylsiloxy)silylpropyl]methacrylamide, tris(pentamethyldisiloxyanyl)-3-methacrylatopropylsilane (T2), and tristrimethylsilyloxysilylpropyl methacrylate (TRIS). An exemplary siloxane-containing monomer is TRIS, which is referred to 3-methacryloxypropyltris(trimethylsiloxy) silane, and represented by CAS No. 17096-07-0. The term "TRIS" also includes dimers of 3-methacryloxypropyltris (trimethylsiloxy) silane.

The hydrophilic monomer can be used in the invention. Suitable hydrophilic monomers include, but are not limited to, hydroxyl-substituted lower alkyl (C1 to C8) acrylates and methacrylates, acrylamide, methacrylamide, (lower allyl) acrylamides and -methacrylamides, ethoxylated acrylates and methacrylates, hydroxyl-substituted (lower alkyl)acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl4,4'-dialkyloxazolin-5-one, 2- and 4-vinylpyridine, vinylically unsaturated carboxylic acids having a total of 3 to 5 carbon atoms, amino(lower alkyl)- (where the term "amino" also includes quaternary ammonium), mono(lower alkylamino)(lower alkyl) and di(lower alkylamino)(lower alkyl)acrylates and methacrylates, allyl alcohol and the like. Among the particularly suitable hydrophilic vinylic monomers are N,N-dimethylacrylamide (DMA), 2-hydroxyethylmethacrylate (HEMA), hydroxyethyl acrylate (HEA), hydroxypropyl acrylate, hydroxypropyl methacrylate (HPMA), trimethylammonium 2-hydroxy propylmethacrylate hydrochloride, dimethylaminoethyl methacrylate (DMAEMA), glycerol methacrylate (GMA), N-vinyl-2-pyrrolidone (NVP), dimethylaminoethylmethacrylamide, acrylamide, methacrylamide, allyl alcohol, vinylpyridine, N-(1, 1-dimethyl-3-oxobutyl)acrylamide, acrylic acid, and methacrylic acid.

Any known suitable vinylic monomer containing at least one functional group selected from the group consisting of hydroxyl group—OH, amino group—NHR (wherein R is hydrogen or C1 to $C_8$ alkyl), carboxylic group—COOH, epoxy group, amide group—CONHR, and combinations thereof can be used as functionalizing vinylic monomer in the present invention. Preferred examples of such vinylic monomers include methacrylic acid (MAA), acrylic acid, glycidylmethacrylate, glycidylacrylate, HEMA, HEA, and N-hydroxymethylacrylamide (NHMA).

The cross-linker may be chosen from, for example, allyl (meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate or diallyl phthalate. A preferred cross-linking agent is ethylene glycol dimethacrylate (EGDMA), ethylene glycol dimethacrylate, trimethyloylpropane trimethacrylate, diethyleneglycol dimethacrylate, bisphenol A dimethacrylate, diglycidyl bisphenol A dimethacrylate, dimethacrylate-terminated polyethylene glycol, a reactive linear or pendant polyether modified silicone, diacrylate or methacrylated silicones or a combination of two or more thereof.

The composition comprises a thermal or a photo initiator, wherein the photo initiator is chosen from peroxides such as benzoyl peroxide, benzoin methyl ether, diethoxyacetophenone, a benzoylphosphine oxide, 1-hydroxycyclohexyl phenyl ketone, 2-hydroxy-2-methyl propiophenone (HMPP), Darocure® types, and Irgacure® types, preferably Darocure®1 173, Irgacure® 4265 and Irgacure® 2959. Azo type initiators (e.g. 2,2'-azobis (2,4-dimethylpentanenitrile), 2,2'-azobis (2-methylpropanenitrile), 2,2'-azobis (2-methylbutanenitrile)) can be used as photo or thermal initiators. Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is azobisisobutyronitrile (AIBN), or a combination of two or more thereof.

The ionically modified silicone is present in an amount of from about 1 weight percent to about 99 weight percent; 5 weight percent to about 90 weight percent 10 weight percent to about 75 weight percent; or 25 weight percent to about 50 weight percent of the hydrogel composition. The ratio of the ionically modified silicone macromer to organic monomer is from about 1:100 to about 100:1. In one embodiment, the ratio of a hydrophilic silicone macromer to a free-radical polymerizable organic monomer is from about 1:99 to 99:1; 1:75 to 75:1; or 1:50 to about 50:1. In one embodiment, the ratio of an ionically modified silicone to a organic monomer is from about 1:10 to about 10:1. In one embodiment, the ratio of an ionically modified silicone to organic monomer is about 1:1.

The composition can be actinically cured to make homopolymers, co-polymers or cross-linked networks. They can also be blended with organic or siloxane monomers, macromers or pre-polymers to obtain hydrogels. The hydrogels described here may be employed in a medical device, medical insert, or contact lens, ocular inserts, etc. The medical device may be formed from the present compositions or may comprise a film or layer formed from the compositions.

Also provided is a drug delivery system comprising the hydrogel comprising the ionically modified silicones and a pharmaceutically active substance associated with the hydrogel material. The drug delivery system may form a medical device itself (e.g., a contact lens) or may be provided as a film or material on a surface of a medical device (e.g., a probe, wand, insert, patch, etc.).

The medical devices have an ionic surface with an overall effective neutral charge. This provides a hydrophilic surface that may attract fewer biomaterials and form less debris on the surface. The ionic moiety with effective neutral charge can also provide inherent antimicrobial properties to the medical device.

The hydrogel composition can be water soluble or water dispersible. The water dispersibility or solubility is enhanced by adding surfactants or solvents which are health care friendly. The hydrogels upon curing can be extracted easily between 5-150° C. to remove unreacted ingredients in an ecofriendly manner. The extraction can be made in the following ways. The hydrogel article can be prepared in water or water miscible solvents and transferred to DI water or buffered aqueous solutions. The articles can be extracted for leachable reactants or additives until desired concentration is reached.

A "lens-forming material" refers to a polymerizable composition (or formulation) which can be cured (i.e., polymerized and/or crosslinked) thermally or actinically to obtain a crosslinked polymer. As used herein, "actinically" in reference to curing or polymerizing of a polymerizable composition or material or a lens-forming material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art. Lens-forming materials are well known to a person skilled in the art. These can also be blended with organic or siloxane monomers, macromers or pre-polymers to obtain hydrogels. The hydrogels may be used to form or coat a medical device, medical insert, contact lens, ocular inserts, etc. The resultant medical device has an ionic surface with an overall effective charge is neutral. This provides a hydrophilic surface that may attract fewer biomaterials and form less debris on the surface. The ionic moiety with an effective neutral charge can also provide inherent antimicrobial properties to the medical device.

As used herein, the term "active ingredient" refers to a material that is biologically active and/or active to light radiation. The active ingredient may be either a reactive ingredient or a non-reactive ingredient. A reactive active ingredient refers to an active ingredient containing a polymerizable ethylenic group attached to active substance. A non-reactive type active ingredient refers to an active ingredient that is biologically or light active but which do not have any group which can be polymerized under the actinic polymerization conditions. Non-reactive active ingredients will penetrate inside or be incorporated within the crosslinked polymer network or polymer chain. This active substance can have functionalities that can form a non-covalent bond with the polymer.

An "interpenetrating polymer network (IPN)" as used herein refers broadly to an intimate network of two or more polymers at least one of which is either synthesized and/or crosslinked in the presence of the other(s). Techniques for preparing IPN are known to one skilled in the art. For a general procedure, see U.S. Pat. Nos. 4,536,554, 4,983,702, 5,087,392, and 5,656,210, the contents of which are all incorporated herein by reference. The polymerization is generally carried out at temperatures ranging from about room temperature to about 145° C.

The method of incorporating non-reactive active ingredients comprises grinding the actives in a solution of a polyionic material preferably to a particle size of 1.5 micrometers or smaller to obtain a dispersion, wherein the concentration of the polyionic material is sufficient to coat pigment particles, preferably from about 0.01% to 20% (wt. vol.); filtering the solution with pigment particles; optionally washing the filtered pigment particles; and optionally drying the filtered pigment particles coated with the one or more polyionic materials. The polycationic material is selected from the group consisting of poly(allylamine hydrochloride), poly(ethyleneimine), poly(vinylbenzyltriamethylamine), polyaniline, sulphonated polyaniline, polypyrrole, poly(pyridinium acetylene), and mixtures thereof, wherein the polyanionic material is selected from the group consisting of polymethacrylic acid, polyacrylic acid, poly(thiophene-3-acetic acid), poly(4-styrenesulfonic acid), sodium poly(styrene sulfonate), poly(sodium styrene sulfonate), and mixtures thereof. A polycationic material used in the present invention can also include polymeric quaternary ammonium compounds (polyquats). When polyquats are used in the coating of an ophthalmic lens, they may impart antimicrobial properties to the ophthalmic lens.

Any standard grinding techniques can be used in the present invention. Suitable mixing devices include, but are not limited to, high speed mixers, Kady Mills, colloid mills, homogenizers, microfluidizers, sonalators, ultrasonic mills, roll mills, ball mills, roller mills, vibrating ball mills, attritors, sand mills, varikinetic dispensers, three-roll mills, Banbury mixers, or other techniques known to those skilled in the art (see Ross S and Morrison I D, Colloidal Systems and Interfaces. New York: John Wiley & Sons, 1988.)

The actives that are active to radiation or light containing reactive groups that may be used alone or in combination are Reactive Black 5 [2,7-naphthalenedisulfonic acid, 4-amino-5-hydroxy-3,6-bis((4-((2-(sulfooxy)ethyl)sulfonyl)phenyl)azo)-tetrasodium salt] (CAS Reg. No. 17095-24-8); Reactive Blue 21 [copper, (29H,31H-phthalocyaninato(2-)-N 29,N 30,N 31,N 32)-, sulfo((4-((2-sulfooxy)ethyl)sulfonyl)phenyl)amino) sulfonyl derivs] (CAS Reg. No. 73049-92-0); Reactive Orange 78 [2-naphthalenesulfonic acid, 7-(acetylamino)-4-hydroxy-3-((4-((2-(sulfooxy)ethyl)sulfonyl)phenyl)azo)-] CAS Reg. No. 68189-39-9); Reactive Yellow 15 [benzensulfonic acid, 4-(4,5-dihydro-4-((2-methoxy-5-methyl-4-((2-(sulfooxy)ethyl) sulfonyl)phenyl)azo)-3-methyl-5-oxo-1H-pyrazol-1-yl)-1 (CAS Reg. No. 60958-41-0); Reactive Blue No. 19 [2-anthracene-sulfonic acid, 1-amino-9,10-dihydro-9,10-dioxo-4-((3-((2-(sulfooxy)ethyl)sulfonyl)phenyl)amino)-, disodium salt] (CAS Reg. No. 2580-78-1); Reactive Blue No. 4 [2-anthracenesulfonic acid, 1-amino-4-(3-((4,6-dichloro-s-triazin-2-yl)amino)-4-sulfoanilino)-9,10-dihydro-9,10-dioxo, disodium salt] (CAS Reg. No. 4499-01-8); C.I. Reactive Red 11 [5-((4,6-dichloro-1,3,5-triazin-2-yl)amino)-4-hydroxy-3-((1-sulfo-2-naphthalenyl)azo)-2,7-naphthalenedisulfonic acid, trisodium salt] (CAS Reg. No. 12226-08-3); C.I. Reactive Yellow 86 [1,3-benzenedisulfonic acid, 4-((5-aminocarbonyl-1-ethyl-1,6-dihydro-2-hydroxy-4-methyl-6-oxo-3-pyridinyl)azo)-6-(4,6-dichloro-1,3,5-triazin-2-yl)amino)-, disodium salt] (CAS Reg. No. 61951-86-8); C.I. Reactive Blue 163 [triphenodioxazinedisulfonic acid, 6,13-dichloro-3,10-bis((4-((4,6-dichloro-1,3,5-triazin-2-yl)amino) sulfophenyl)amino)-, tetrasodium salt] (CAS Reg. No. 72847-56-4); and C.I. Reactive Red 180 [5-(benzoylamino)-4-hydroxy-3-((1-sulfo-6-((2-(sulfooxy)ethyl)sulfonyl)-2-naphthalenyl)azo)-2,7-naphthalenedisulfonic acid, tetrasodium salt] (CAS Reg. No. 98114-32-0).

Natural dyes are dyes or colorants derived from plants, invertebrates, or minerals. The majority of natural dyes are vegetable dyes from plant sources—roots, berries, bark, leaves, and wood—and other organic sources such as fungi and lichens. The natural dyes such as paprika, Curcumin and chlorophyll can also be used as a non-reactive active substance. The methacrylation of paprika, Curcumin and chlorophyll lead to reactive form of natural dyes and can be used in the hydrogel composition.

In one embodiment the actives can be pharmaceutically active substances used in medical science. The pharmaceutically active substance may be physiologically active materials or medicinal drugs (e.g., agents affecting the central nervous system, antiallergic agents, cardiovascular agents, agents affecting respiratory organs, agents affecting digestive organs, hormone preparations, agents affecting metabolism, antitumor agents, antibiotic preparations, chemotherapeutics, antimicrobials, local anesthetics, antihistaminics, antiphlogistics, astringents, vitamins, antifungal agents, peripheral nervous anesthetics, vasodilators, crude drug essences, tinctures, crude drug powders, hypotensive agents, immunosuppressants, etc.). These may include, but are not limited to antimicrobial, antibacterial, medicinal, etc., substances.

Particularly suitable actives are those related to ophthalmic area. The ophthalmic actives delivery formulation is especially suitable for use with any of the ophthalmically active drugs, particularly amine drugs known for use in the treatment of diseases of the eye, such as glaucoma. These ophthalmic drugs include pilocarpine, epinephrine, tetracycline, phenylephrine, eserine, phospholine iodide, demecarium bromide, cyclopentolate, homatropine, scopolamine, chlortetracycline, bacitracin, neomycin, polymixin, gramicidin, oxytetracycline, chloramphenicol, gentamycin, penicillin, erythromycin, carbachol, sulfacetamide, polymixin B, idoxuridine, isoflorophate, fluoromethalone, dexamethasone, hydrocortisone, hydrocortisone acetate, dexamethasone 21-phosphate, fluorocinolone, medrysone, prednisolone, methyl prednisolone, prednisolone 21-phosphate, prednisolone acetate, betamethasone, Ibuprofen, Flurbiprofen, Cloricromene, Diclofenac diethyl ammonium, Piroxicam, Methylprednisolone, ketotifen, moxifloxacin and triamcinolone. Ophthalmically, optically or nasally acceptable pharmaceutically active compound having a cationic nature in an aqueous medium in the pH range of from 3.0 to 8.5. The most preferred basic actives are betaxolol, timolol, and dipivefrin. The compositions of the present invention may contain two or more basic active components in combination. The basic active component is present at a level of about 0.01 to 4.0%, preferably from 0.10 to 1.0%.

The ophthalmic drug or active is present in the hydrogel compositions at a level effective to accomplish the purpose of the drug. Usual levels of use of the ophthalmic drug are in the range of from about 0.03 to about 15 percent by weight of the hydrogel composition. These actives can be used in the formulations as such or by mixing with polymers, ionic polymers, or surfactants A polymeric suspending material can be used to disperse the actives and can be added as an additive in the above said hydrogel compositions. The polymeric suspending component contained in the compositions of the present invention can consists essentially of a combination of a carboxyvinyl polymer and a polymer selected from the group consisting of hydroxyethyl cellulose; hydroxypropyl cellulose; and carboxymethyl cellulose, cyclodextrins, poly(vinyl alcohol), poly(vinyl pyrrolidone), poly(ethylene glycol), poly(dimethylsiloxane) and so on.

Pharmaceutically active substances can also be associated with the hydrogel by other methods such as imbibing or molecular imprinting. In imbibing, the hydrogel is soaked in a solution of the pharmaceutically active substance. The hydrogel imbibes the pharmaceutically active substance. The hydrogel releases the pharmaceutically active substance upon being disposed in or contacting the target environment, e.g., injection, ingestion, insertion (for example by insertion of a contact lens formed from the hydrogel into the eye).

In one embodiment, the ophthalmically active ingredients can leach out slowly from the polymer and maintain the critical concentration around the article to give desired pharmaceutical activity.

Kits or systems for making hydrogels may be prepared. The kits are manufactured using medically acceptable conditions and contain precursors (e.g., compounds of Formula (I) along with other reactive components such as monomers, crosslinkers, etc.) that have sterility, purity and preparation that is pharmaceutically acceptable. The kit may contain an applicator as appropriate, as well as instructions. A therapeutic agent may be included pre-mixed or available for mixing. Solvents/solutions may be provided in the kit or separately, or the components may be pre-mixed with the solvent. The kit may include syringes and/or needles for mixing and/or delivery.

In some embodiments, kits having precursors and other materials as needed to form a hydrogel in situ with a therapeutic agent may be provided, with the component parts including those described herein. The hydrogel may be easily removable or self-removing, and can be biodegradable or suited to delivery to easily accessible areas without dispersal. It can be made so it is easy to mix and use, with an option to combine all the precursors in a single container. The hydrogel may be made with safe, all-synthetic materials. The degradation and/or delivery rate may be controlled to fit the time periods described. Patient compliance may be enhanced by avoiding repeated dosing. Similarly kits with an applicator may be made that include a material as set forth herein, e.g., a preformed dehydrated hydrogel.

The hydrogel material may also be used in connection with a medical device. The hydrogel material may be provided as a film on a surface or area of a medical device that may be used to deliver a pharmaceutically active material to a patient and/or provide a property to the device (e.g., antibiotic or antimicrobial). For example, the hydrogel film with the pharmaceutically active agent could be provide at the tip of a wand or probe that may be inserted in to the patient such that the pharmaceutically active agent may be delivered to the patient. In another embodiment, the hydrogel film could be provided as part of a layer of a patch (e.g., a medicinal patch or Band-Aid) that may be placed on a patient to deliver a medicament or drug to a patient.

The present hydrophilic silicone compounds can be used in a variety of applications including as a film forming additive in a textile, paper, leather, personal care, health care, home care, coating, painting or seed treatment formulations.

EXAMPLES

Equilibrium Water Content

The film is immersed in buffer of pH 6.5-8.5 (chosen based on the ionic types) for 48 hours. Then the surface water is wiped off gently using lintless tissue paper. The hydrated film is weighed precisely and then dried in solid content analyzer at 150° C. for 15 minutes and weighed again for dry weight. Water content is calculated based on weight change using the following equation.

Water Wettability $$\% \text{ Water content} = \frac{[\text{Weight of hydrated lens} - \text{Weight of dry lens}]}{\text{Weight of hydrated lens}} \times 100\%$$

Water wettability is measured according to: Neumann A W, Godd R J. Techniques of measuring contact angles. In: Good R J, Stromberg R R, Editors. Surface and Colloid science—Experimental methods, vol. 11. New York: Plenum Publishing; (1979), pp. 31-61.

Water wettability of the film surface is evaluated by measuring contact angle using Tracker TECLIS goniometer. In a static contact angle method the wet film is first pressed with lintless tissue paper and then a drop of water is placed on the surface. The contact angle is measured using a goniometer. Lower contact angle values represent a greater degree of hydrophilicity or better surface wettability of the film.

Actives Delivery

Active Loading Experiments

Pharmaceutically active loaded films are prepared by method that comprises hydrogel films and drug solution in phosphate buffer (renu solution).

Imbibition method include steps: 0.3 g of the hydrogel film was imbibed in 2 ml of the drug solution (3% w/w) for 24 h.

In another method, drug imprinted lens film was prepared by mixing 6% ww of the drug in the hydrogel formulation. The resultant clear, homogeneous solution was poured into PET (poly(ethylene terephthalate)) to a measuring gap of 1 mm. The formulation was cured by exposure to UV irradiation of 105 mW/cm$^2$ for 20-180 seconds. After polymerization, the film was washed with isopropanol to remove unreacted monomers. Then washing was done with deionized distilled water and 0.9% NaCl solutions to remove the template drug. The complete removal of timolol was ensured by analyzing the washing solutions spectrophotometrically. Resulting film was imbibed in 2 ml of the drug solution (3% w/w) for 24 h for drug uptake.

Active Release by HPLC

High Performance Liquid Chromatography (HPLC): HPLC method is optimized for quantification of drug released from polymer matrix by considering the polar nature of drug and sample matrix. The solvent conditions were optimized employing a water (0.02% H3PO4)/Acetonitrile solvent mixture with a gradient of 10-90% of acetonitrile in 0 to 5 min. to produce narrow and symmetrical peak for drug analytes. The drug aliquots collected at different time intervals were analyzed on Shimadzu Prominence LC 20AD system using column Extend C18, 150×4.6 mm, 5 µm kept at 40° C., sample was injected under flow rate of 1 mL/min. with injection volume of 5 uL. For quantification process, the drug concentration monitored with UV detector at 300 nm, external calibration plots were generated for respective drug with series of standard solutions varying concentration in the range of 10-500 ppm. The drug response found to be linear, the standard curves used for calculation of unknown drug concentration in samples.

Modulus

The Young's modulus of the hydrated film is measured using an Instron tensile tester. The wet samples are cut into 6 cm×0.8 cm strips and the mechanical properties are measured with a load cell of 50 N and crosshead speed of 10 mm/minute. The modulus is determined from the initial slope of a stress-strain curve. Modulus is directly correlated to the softness of the material. Lower the modulus, softer is the material.

Example 1: Synthesis of 4-(2(-acryloyloxy)-4-(2-(1,1,1,3,5,5,5-heptamethyltrisiloxane-3-yl)ethyl)cyclohexyl)oxy-4-oxabutanoic acid A round-bottom flask equipped with a stirring bar, reflux condenser, and dropping funnel was charged with 100 grams of vinyl cyclohexyl epoxy functionalized trisiloxane, and toluene, and the reaction mixture was heated to 70-75° C. At this point, a catalytic amount of Titanium isopropoxide and TEMPO (2,2,6,6-Tetramethylpiperidine 1-oxyl) was added, and the reaction mixture was further heated to 90° C. To this reaction mixture, 21 grams of acrylic acid was added gradually. After completion, the reaction mixture was passed over Dowex-WBA resin to remove unreacted acrylic acid. The product was decolorized using activated charcoal and filtered over celite bed. The filtrate was vacuum stripped to yield a pale yellow color product, 5-(2-(1,1,1,3,5,5,5,-heptamethyltrisiloxane-3-yl)ethyl)-2-hydroxycyclohexylacrylate.

5-(2-(1,1,1,3,5,5,5,-heptamethyltrisiloxane-3-yl)ethyl)-2-hydroxycyclohexylacrylate (50 grams), Toluene, and succinic anhydride (18 grams) were further charged into a round bottom flask equipped with stirring bar, reflux condenser, and nitrogen inlet. To this, triethylamine and hydroquinone were added as catalyst and radical scavenger, respectively, and the reaction mixture was heated to 60-65° C. After completion, the product was vacuum striped, re-dissolved in chloroform, and washed with brine solution. The organic phase was passed over a Tulsion T66-MP resin to remove traces of Triethylamine and decolorized using activated charcoal. The organic layer was concentrated after removal of charcoal to yield a pale yellow color viscous product.

Example 2: Synthesis of (4-(((2-(acryloyloxy)-5-(2-(1,1,1,3,5,5,5-heptamethyltrisiloxan-3-yl)ethyl)cyclohexyl)oxy)-4-oxobut-2-enoic acid 5-(2-(1,1,1,3,5,5,5,-heptamethyltrisiloxane-3-yl)ethyl)-2-hydroxycyclohexylacrylate (50 grams), Toluene, and maleic anhydride (18 grams) were further charged into a round bottom flask equipped with a stirring bar, reflux condenser, and nitrogen inlet. To this Triethylamine and Hydroquinone were added as catalyst and radical scavenger respectively and the reaction mixture was heated to 60-65° C. After completion, the product was vacuum striped, re-dissolved in chloroform, and washed with brine solution. The organic phase was passed over Tulsion T66-MP resin to remove traces of Triethylamine and decolorized using activated charcoal. The organic layer was concentrated after removal of charcoal to yield a pale yellow color viscous product.

Example 3: Synthesis of 3-(((—2-(acryloyloxy)-5-(2-(1,1,1,3,5,5,5-heptamethyltrisiloxan-3-yl)ethyl)cyclohexyl)oxy)carbonyl)but-3-enoic acid A round bottom flask equipped with a stir bar, reflux condenser, and nitrogen inlet was charged with 5-(2-(1,1,1,3,5,5,5,-heptamethyltrisiloxane-3-yl)ethyl)-2-hydroxycyclohexylacrylate (50 grams) and Toluene. To this, Triethylamine and Hydroquinone were added as catalyst and radical scavenger, respectively, and the reaction mixture was heated to 60-65° C. To this, itaconic anhydride (20 grams) was added gradually. After completion, the product was vacuum striped, re-dissolved in chloroform, and washed with brine solution. The organic phase was passed over Tulsion T66-MP resin to remove traces of Triethylamine and decolorized using activated charcoal. The organic layer was concentrated after removal of charcoal to yield a pale yellow color viscous product.

Example 4: Synthesis of 4-((5-(2-(1,1,1,3,5,5,5-heptamethyltrisiloxan-3-yl)ethyl)-2-(2-methacrylamidoacetoxy)cyclohexyl)oxy)-4-oxobutanoic acid A round-bottom flask equipped with a stirring bar, reflux condenser, and dropping funnel was charged with vinyl cyclohexyl epoxy functionalized trisiloxane (25 grams) Methyl ethyl ketone, and TEMPO (2,2,6,6-Tetramethylpiperidine 1-oxyl and the reaction mixture was heated to 75-80° C. At this point a pinch of glycine methacrylate and catalytic amount of titanium isopropoxide was added, and the reaction mixture was further heated to 80° C. To this reaction mixture, glycine methacrylate (10 grams) was added gradually. After completion, the product was isolated, re-dissolved in ethyl acetate, and the organic layer was washed with brine. The organic layer was concentrated to yield a pale yellow color product, 4-(2-(1,1,1,3,5,5,5-heptamethyltrisiloxan-3-yl)ethyl)-2-hydroxycyclohexyl 2-methacrylamido acetate 4-(2-(1,1,1,3,5,5,5-heptamethyltrisiloxan-3-yl)ethyl)-2-hydroxycyclohexyl 2-methacrylamidoacetate (15 gms), Toluene, and succinic anhydride (4.6 grams) were further charged into a round bottom flask equipped with a stirring bar, reflux condenser, and nitrogen inlet. To this, Triethylamine and Hydroquinone were added as catalyst and radical scavenger, respectively, and the reaction mixture was heated to 60-65° C. After completion the product was vacuum striped, re-dissolved in chloroform and washed with brine solution. The organic phase was passed over Tulsion T66-MP resin to remove traces of Triethylamine and decolorized using activated charcoal. The organic layer was concentrated after removal of charcoal to yield a pale yellow color viscous product.

Example 5: Synthesis of 4-((2-(methacryloyloxy)-4-ethylcyclohexyl)oxy)-4-oxobutanoic acid functionalized polydimethylsiloxane A round-bottom flask equipped with a stirring bar, reflux condenser, and dropping funnel was charged with 1.6 g of 4-vinyl-1-cyclohexene 1,2-epoxide, and was heated to 70-75° C. At this point, a catalytic amount of platinum(0)-1,3-divinyl-1,1,3,3-tetramethyldisiloxane complex solution in xylene, (Pt around 2%) was added and the reaction mixture was further heated to 90° C. To this reaction mixture, 10 grams of monohydride functionalized polydimethylsiloxane, was added drop wise. After completion, the reaction mixture was cooled down to 70-75° C. and 20 ml of Toluene and a catalytic amount of Titanium isopropoxide along with TEMPO were added and the reaction mixture was further heated to 90° C. To this reaction mixture, 2 grams of methacrylic acid was added dropwise over a period of 2 h. The reaction was monitored using $^1$H-NMR spectroscopy. After completion of the reaction, the mixture was cooled down to 50° C. and succinic anhydride (4.6 grams) along with Triethylamine were further charged into the flask. The reaction mixture was heated to 60-65° C. for 12 hours. After completion, solvent was vacuum stripped, crude product was re-dissolved in dichloromethane and washed with hot brine solution. The organic phase was passed over Tulsion T66-MP resin to remove traces of trimethylamine and decolorized using activated charcoal. The organic layer was filtered over Celite column to remove charcoal and then stirred along with Dowex-WBA resin to remove unreacted methacrylic acid. The organic phase was further filtered and concentrated to yield pale yellow colored viscous product. The product was characterized via NMR and HPLC techniques.

Example 6: Synthesis of Charge Neutral Complexes of Silicone Carboxylates

A charge neutral complex is formed by mixing an equimolar mixture of a sodium salt of the silicone carboxylic acid of Example 3 and a quaternary ammonium group (methacrylatoethyl trimethyl ammonium chloride) containing reactive or non-reactive organic or silicone based material is used to form a charge neutral complex of silicones. This complex is purified by precipitation method as per the need.

Example 7: Synthesis of Charge Neutral Complexes of Silicone Carboxylic Acids An equimolar mixture of the silicone carboxylic acid of Example 3 and an amine group (3-Aminopropyl)tris(trimethylsiloxy)silane, 2-aminoethylmethacrylate containing reactive or non-reactive organic or silicone based material is used to form a charge neutral complex of silicones. This complex is purified by precipitation method as per the need.

Example 8: Synthesis of Charge Neutral Complexes of Silicone Carboxylic Acids or Carboxylates with Polyionic Polymers The sodium salt of the silicone carboxylic acid of Example 3 is mixed with a cationic polymer containing cationic groups to make the complex material. The cationic polymer containing group is a N,N'-bis(3-aminopropyl)-1, 4-diaminobutane, poly(ethyleneimine) solution with MW 1200-60000, poly(styrene sulfonate)-poly(ethyleneimine) complex.

Example 9: Synthesis of Charge Neutral Complexes of Silicone Carboxylic Acids or Carboxylates A charge neutral complex of silicones prepared in example 5 and 6 are mixed with active substances. This complex is purified by precipitation method as per the need or used as it is.

Example 10: Synthesis of Charge Neutral Complexes of Silicone Carboxylic Acids or Carboxylates with Actives Using Polyionic Polymers The sodium salt of the silicone carboxylic acid of Example 3 is mixed with cationic polymers or cationic polymer blends with active molecules containing carboxylate groups were mixed together to make the active loaded complex material. The cationic polymer material is a poly (ethyleneimine) solution with MW 1200-60000, diethylaminoethyl)dextran, poly [2-(N,N-dimethylamino)ethyl methacrylate, poly(l-lycine).

Example 11: Synthesis of Charge Neutral Complexes of Silicone Carboxylic Acids or Carboxylates with Actives The sodium salt of the silicone carboxylic acid or carboxylate of Example 3 is mixed with the active substance ciprofloxacin hydrochloride to make the complex material.

Example 12: Synthesis of Charge Neutral Complexes of Silicone Carboxylates

A charge neutral complex is formed by mixing an equimolar mixture of silicone carboxylic acid of Example 11 and trimethylamine. This complex formation was observed by shift in the peaks in proton NMR.

Example 13: Synthesis of Charge Neutral Complexes of Silicone Carboxylates

A charge neutral complex is formed by mixing an equimolar mixture of silicone carboxylic acid of Example 11 and N-butyl dimethylamine. This complex formation was observed by shift in the peaks in proton NMR.

Example 14: Synthesis of Charge Neutral Complexes of Silicone Carboxylates

A charge neutral complex is formed by mixing silicone carboxylic acid of Example 11 and allylamine in a ratio 3:1. This complex formation was observed by shift in the peaks in proton NMR.

Example 15: Synthesis of Charge Neutral Complexes of Silicone Carboxylates

A charge neutral complex is formed by mixing an equimolar mixture of silicone carboxylic acid of Example 11 and a quaternary ammonium group (benzyl trimethylammonium chloride).

Formation of charge neutral complexes is confirmed from the shift of broad peak of —COOH as well sharp peaks of alkyl groups of amine functionality in 1H NMR spectra. Difference in peak shift values is shown in Table 1.

TABLE 1

$^1$H NMR shifts upon charge neutral complex formation

| | δ —COOH/R$_3$N$^+$H (br) | Shift in amine peaks (ppm) |
|---|---|---|
| Example 5 | 3.31 | |
| Example 12 | 3.86 | 0.1 |
| Example 13 | 4.74 | 0.05 |
| Example 14 | 3.31 | 0.04 |

Example of Non Ionic Silicone

As a comparative example to ionic functionalized silicone for example 5, non-ionic functionalized silicone was synthesized and examined for active uptake and release studies.

Example 16 (Comparative Example): Synthesis of 4-((2-(methacryloyloxy)-4-ethylcyclohexyl) hydroxyl functionalized polydimethylsiloxane A round-bottom flask equipped with a stirring bar, reflux condenser, and dropping funnel was charged with 1.6 g of 4-vinyl-1-cyclohexene 1,2-epoxide, and was heated to 70-75° C. At this point, a catalytic amount of platinum(0)-1,3-divinyl-1,1,3,3-tetramethyldisiloxane complex solution in xylene, (Pt around 2%) was added and the reaction mixture was further heated to 90° C. To this reaction mixture, 10 grams of monohydride functionalized polydimethylsiloxane, was added drop wise. After completion, the reaction mixture was cooled down to 70-75° C. and 20 ml of Toluene and a catalytic amount of Titanium isopropoxide along with TEMPO were added and the reaction mixture was further heated to 90° C. To this reaction mixture, 2 grams of methacrylic acid was added dropwise over a period of 2 h. The reaction was monitored using $^1$H-NMR spectroscopy. After completion of the reaction, the cooled product was stirred overnight with Dowex-WBA resin to remove unreacted methacrylic acid. The organic phase was further filtered and concentrated to yield pale yellow colored viscous product. The product was characterized via NMR and HPLC techniques.

Examples of Hydrogel Films

Selected hydrogel films (listed in Tables 2, 3, and 4) were prepared using materials described in example 1 to 16 along with other organic monomers such as 2-hydroxyethyl methacrylate (HEMA), N,N-dimethyl acrylamide (DMA), N-vinylpyrrolidone (NVP) and crosslinkers such as ethylene glycol dimethacrylate (EGDMA). Other additives used in the formulations were polyvinylpyrrolidone (PVP). The films were cured using 2-hydroxy-2-methyl propiophenone as radical initiator (0.5 wt. %). The resultant clear, homogeneous solution was poured into PET (poly(ethylene terephthalate)) to a measuring gap of 1 mm. The formulations were cured by exposure to UV irradiation of 105 mW/cm$^2$ for 20-180 seconds. Obtained film was immersed in IPA to leach out unreacted monomers after which it was immersed in water. Resulting hydrogel films were evaluated for equilibrium water content, water wettability, actives delivery, modulus and clarity.

TABLE 2

Hydrogel film formulations

| FORMULATION | Example 5 | HEMA | DMA | NVP | EGDMA | HMPP | PVP in IPA (wt %) |
|---|---|---|---|---|---|---|---|
| Example 17 | 100 | | | | 1 | 0.25 | |
| Example 18 | 90 | | 10 | | 1 | 0.25 | |
| Example 19 | 75 | | 25 | | 1 | 0.25 | |
| Example 20 | 50 | | 50 | | 1 | 0.25 | |
| Example 21 | 80 | 20 | | | 1 | 0.25 | |
| Example 22 | 50 | 50 | | | 1 | 0.25 | |
| Example 23 | 75 | 12.5 | 12.5 | | 1 | 0.25 | |
| Example 24 | 63 | | 37 | | 1 | 0.25 | |
| Example 25 | 70 | 10 | 20 | | 1 | 0.25 | |
| Example 26 | 70 | 10 | 20 | | 1 | 0.25 | 6 |
| Example 27 | 75 | 5 | 20 | | 1 | 0.25 | |
| Example 28 | 70 | | 20 | 10 | 1 | 0.25 | |

TABLE 3

Hydrogel film formulations

| FORMULATION | Example 15 | HEMA | DMA | EGDMA | HMPP | PVP in IPA (Wt. %) |
|---|---|---|---|---|---|---|
| Example 29 | 70 | 10 | 20 | 1 | 0.25 | 6 |
| Example 30 | 60 | 20 | 20 | 1 | 0.25 | 6 |

TABLE 4

Hydrogel film formulation

| FORMULATION | Example 16 | HEMA | DMA | NVP | EGDMA | HMPP | PVP in IPA (Wt. %) |
|---|---|---|---|---|---|---|---|
| Example 31 | 70 | 10 | 20 | | 1 | 0.25 | 6 |

Water Content of Hydrogel Film

Example 32. Water content of the hydrogel film can be controlled by varying the composition of the monomers as in examples 17 to 31, for which water content varies from 3-72% as represented in Table 5.

TABLE 5

Percentage water content in the lens films

| FORMULATION | H$_2$O content (±2) |
|---|---|
| Example 17 | 3 |
| Example 18 | 10 |
| Example 19 | 13 |
| Example 20 | 56 |
| Example 21 | 23 |
| Example 22 | 26 |
| Example 23 | 33 |
| Example 24 | 52 |

TABLE 5-continued

Percentage water content in the lens films

| FORMULATION | H$_2$O content (±2) |
|---|---|
| Example 25 | 35 |
| Example 26 | 42 |
| Example 27 | 25 |
| Example 28 | 58 |
| Example 29 | 65 |
| Example 30 | 72 |
| Example 31 | 29 |

Contact Angle Measurements

Example 33. A 0.5 mm thickness film in Example 26 was evaluated for wettability studies using contact angle measurements. The measurement shows contact angle of 65 degree using sessile drop method.

Modulus Studies

Example 34. A lens film of thickness 0.8 mm and length 30 mm of Example 26 was examined for modulus studies. A plot of stress vs strain gives the value of young's modulus of 0.78 MPa.

Examples of Active Release

Actives used in the examples are listed below in Table 6.

TABLE 6

Actives used for delivery

| ACTIVE | DISEASE | LOADING METHOD | RELEASE CONDITION |
|---|---|---|---|
| Timolol Maleate | anti-allergic | Imbibition and Molecular | Media: phosphate buffered saline (PBS) solution |
| Moxifloxacin | antibiotic | | |

TABLE 6-continued

Actives used for delivery

| ACTIVE | DISEASE | LOADING METHOD | RELEASE CONDITION |
|---|---|---|---|
| hydrochloride monohydrate | | Imprinting | Temperature: room temperature |
| Ketotifen fumarate | glaucoma | | |
| Travoprost | glaucoma | | |

Example 36. Timolol Maleate Uptake Studies Upon Film Imbibition

Active loading of timolol maleate in hydrogel film of Example 26 and Example 31 with time of imbibition is shown in FIG. 1.

Figure 2:
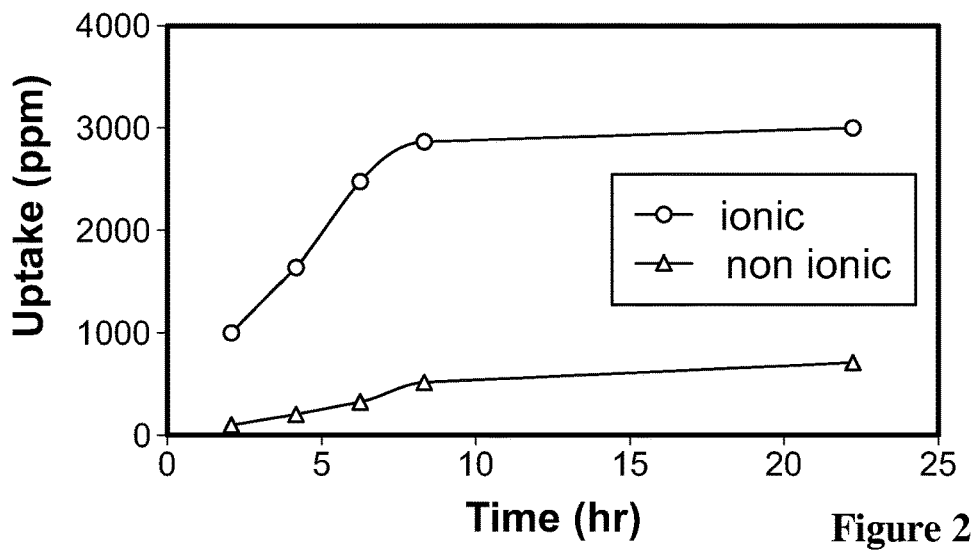
FIG. 2. is a graph illustrating the uptake of Moxifloxacin hydrochloride monohydrate with time.

Example 37. Moxifloxacin Hydrochloride Monohydrate Uptake Studies Upon Film Imbibition Active loading of moxifloxacin hydrochloride monohydrate in hydrogel film of Example 26 and Example 31 with time of imbibition is shown in FIG. 2.

Example 38. Ketotifen Fumarate Uptake Studies Upon Film Imbibition

Figure 3:
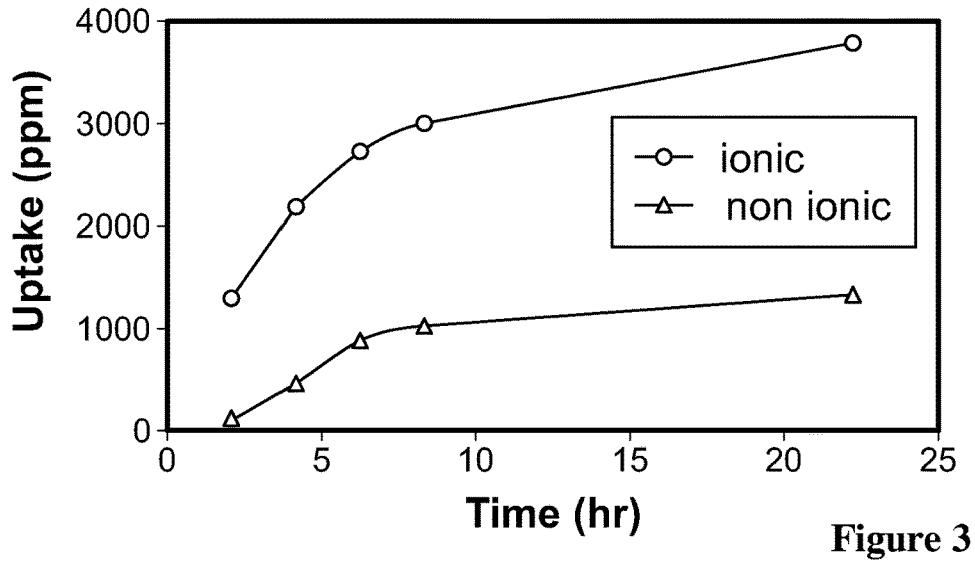
FIG. 3. is a graph illustrating the uptake of Ketotifen fumarate with time.

Active loading of Ketotifen fumarate in hydrogel film of Example 26 and Example 31 with time of imbibition is shown in FIG. 3.

Higher drug loading as well increase in drug uptake with longer imbibition time is observed for hydrogel film bearing functional ionic moieties as opposed to non-functional hydrogel film. Ionic interaction of functional monomers in the hydrogel film with ionic drugs shows better binding to the drugs.

Example 39. Timolol Maleate Release from Drug Imbibed Films

Figure 4:
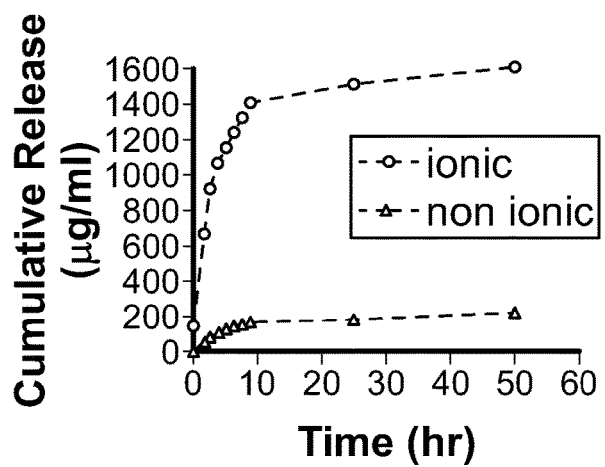
FIG. 4. is a graph illustrating the release of Timolol maleate from the hydrogel film of Example 34 and Example 35.
Figure 4:
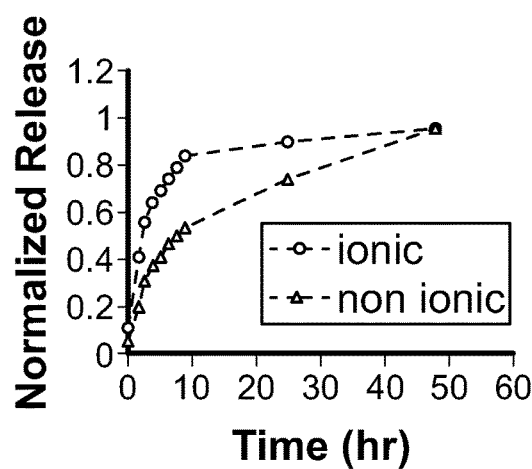

Active loading of timolol maleate in hydrogel film of Example 26 and Example 31 after 24 h of imbibition is shown in Table 7. Release of the drug was tested by immersing the drug loaded film in 2 ml of phosphate buffered saline (PBS) (pH=7.4). An aliquot of 0.5 ml of the solution was sampled and replaced with fresh solution at predetermined intervals. The amount of drug released in the media was measured using HPLC techniques. Cumulative and its normalized drug concentration was calculated and plotted as a function of respective time of sampling which shows a gradual release for a long period of time (>24 hours) as shown in FIG. 4. Total percentage release of the timolol after 48 h is listed below in the table.

TABLE 7

Uptake and percentage release of Timolol maleate

| Example | Uptake (ppm) | % release |
|---|---|---|
| Example 26 | 5873 | 30 |
| Example 31 | 5730 | 4 |

Figure 5:
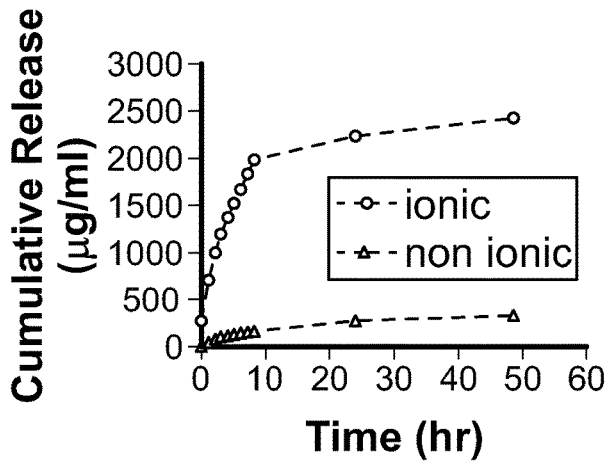
FIG. 5. is a graph illustrating the release of Moxifloxacin hydrochloride monohydrate from the hydrogel film of Example 36 and Example 37.
Figure 5:
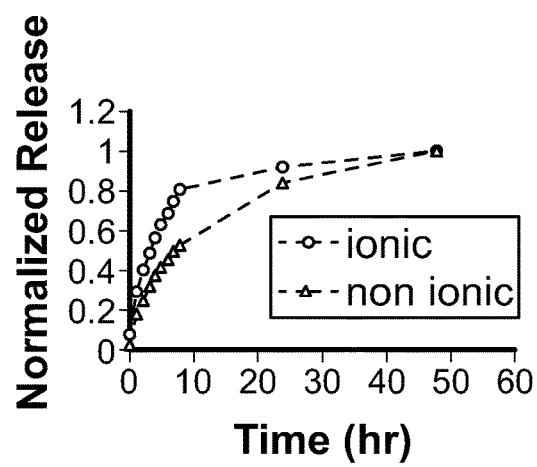

Example 40. Moxifloxacin Hydrochloride Monohydrate Release from Drug Imbibed Films Active loading of Moxifloxacin in hydrogel film of Example 26 and Example 31 after 24 h of imbibition is shown in Table 8. Release of the drug was tested by immersing the drug loaded film in 2 ml of phosphate buffered saline (PBS) (pH=7.4). An aliquot of 0.5 ml of the solution was sampled and replaced with fresh solution at predetermined intervals. The amount of drug released in the media was measured using HPLC techniques. Cumulative and its normalized drug concentration was calculated and plotted as a function of respective time of sampling which shows a gradual release for a long period of time (>24 hours) as shown in FIG. 5. Total percentage release of the moxifloxacin after 48 h is listed below in the table.

TABLE 8

Uptake and percentage release of Moxifloxacin hydrochloride monohydrate

| Example | Uptake (ppm) | % release |
|---|---|---|
| Example 26 | 4756 | 50 |
| Example 31 | 1243 | 26 |

Example 41. Ketotifen Fumarate Release from Drug Imbibed Films

Figure 6:
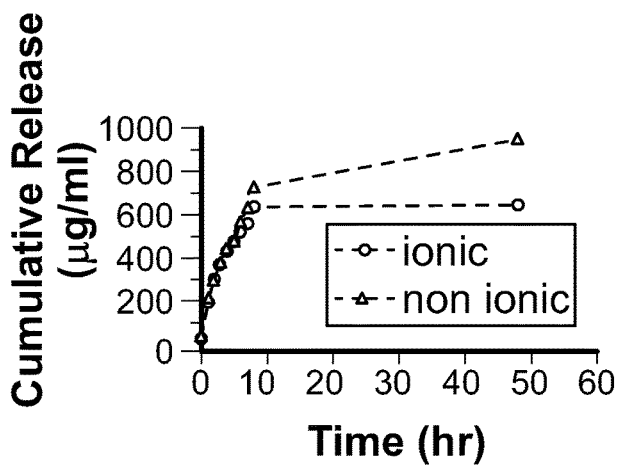
FIG. 6. is a graph illustrating the release of Ketotifen fumarate from the hydrogel film of Example 38 and Example 39.
Figure 6:
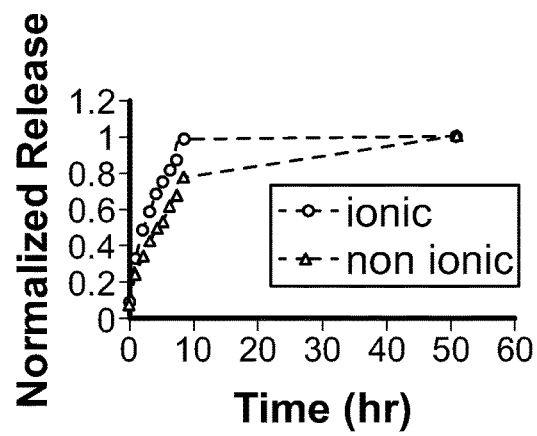

Active loading of ketotifen in hydrogel film of Example 26 and Example 31 after 24 h of imbibition is shown in Table 9. Release of the drug was tested by immersing the drug loaded film in 2 ml of phosphate buffered saline (PBS) (pH=7.4). An aliquot of 0.5 ml of the solution was sampled and replaced with fresh solution at predetermined intervals. The amount of drug released in the media was measured using HPLC techniques. Cumulative and its normalized drug concentration was calculated and plotted as a function of respective time of sampling which shows a gradual release for a long period of time (>24 hours) as shown in FIG. 6. Total percentage release of the ketotifen after 48 h is listed below in the table.

TABLE 9

Uptake and percentage release of Ketotifen fumarate

| Example | Uptake (ppm) | % release |
|---|---|---|
| Example 26 | 4270 | 16 |
| Example 31 | 2341 | 40 |

Example 42. Timolol Maleate Release from Molecular Imprinted Films

Figure 7:
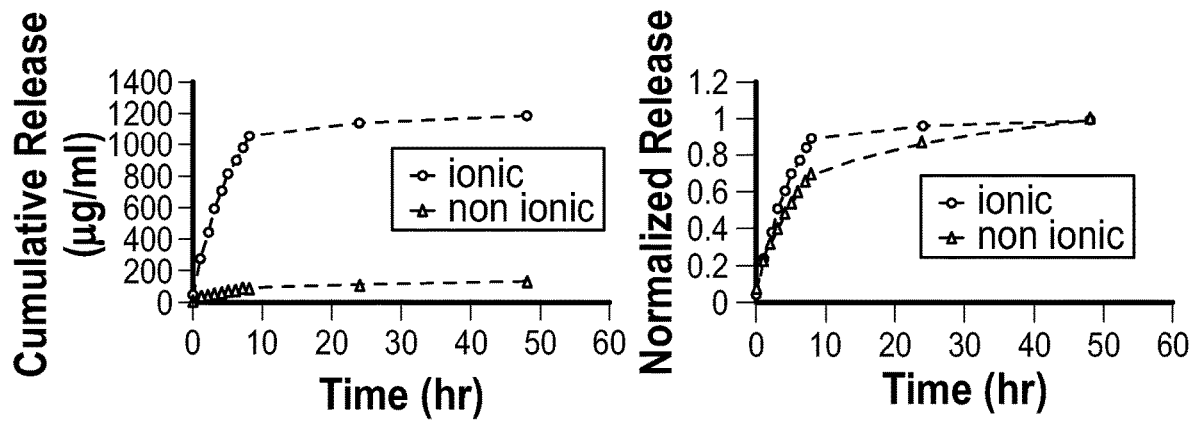
FIG. 7. is a graph illustrating the release of Timolol maleate from the hydrogel film of Example 42 and Example 43.

Active loading of timolol in molecular imprinted hydrogel film of Example 26 and Example 31 after 24 h of imbibition is shown in Table 10. Release of the drug was tested by immersing the drug loaded film in 2 ml of phosphate buffered saline (PBS) (pH=7.4 An aliquot of 0.5 ml of the solution was sampled and replaced with fresh solution at predetermined intervals. The amount of drug released in the media was measured using HPLC techniques. Cumulative and its normalized drug concentration was calculated and plotted as a function of respective time of sampling which shows a gradual release for a long period of time (>24 hours)

as shown in FIG. 7. Total percentage release of the timolol after 48 h is listed below in the table.

TABLE 10

Uptake and percentage release of Timolol maleate

| Example | Uptake (ppm) | % release |
|---|---|---|
| Example 26 | 1225 | 98 |
| Example 31 | 160 | 86 |

Figure 8:
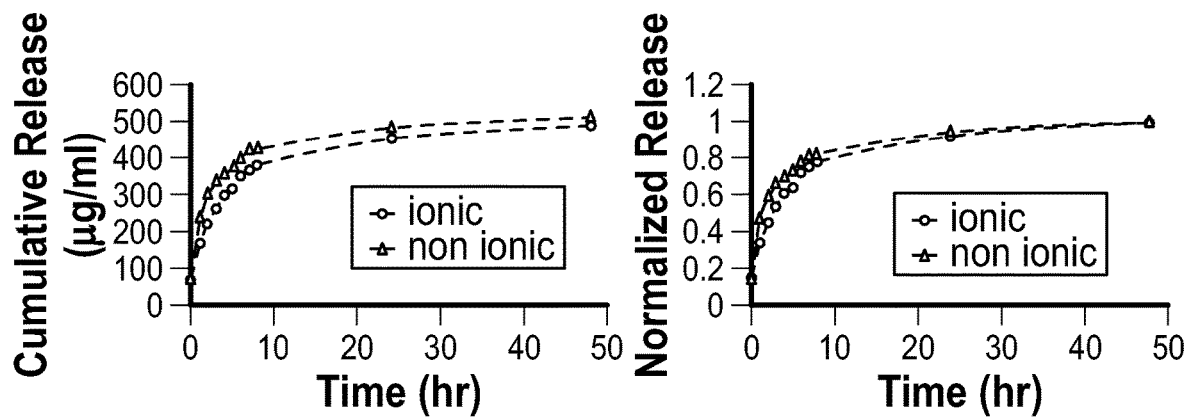
FIG. 8. is a graph illustrating the release of Moxifloxacin hydrochloride monohydrate from the hydrogel film of Example 44 and Example 45.

Example 43. Moxifloxacin Hydrochloride Monohydrate Release from Molecular Imprinted Films Active loading of Moxifloxacin in hydrogel film of Example 26 and Example 31 after 24 h of imbibition is shown in Table 11. Release of the drug was tested by immersing the drug loaded film in 2 ml of phosphate buffered saline (PBS) (pH=7.4). An aliquot of 0.5 ml of the solution was sampled and replaced with fresh solution at predetermined intervals. The amount of drug released in the media was measured using HPLC techniques. Cumulative and its normalized drug concentration was calculated and plotted as a function of respective time of sampling which shows a gradual release for a long period of time (>24 hours) as shown in FIG. 8. Total percentage release of the moxifloxacin after 48 h is listed below in the table.

TABLE 11

Uptake and percentage release of Moxifloxacin hydrochloride monohydrate

| Example | Uptake (ppm) | % release |
|---|---|---|
| Example 26 | 486 | 100 |
| Example 31 | 464 | 100 |

Example 44. Ketotifen Fumarate Release from Molecular Imprinted Films

Figure 9:
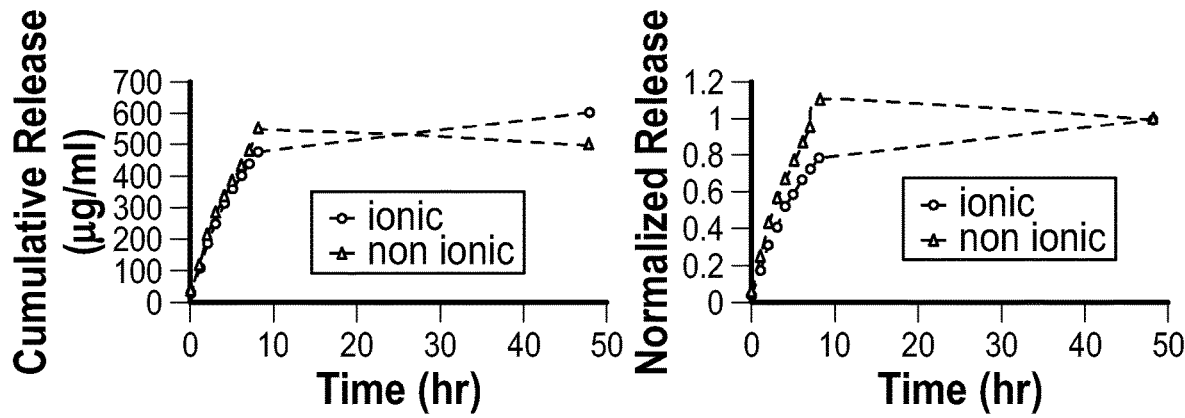
FIG. 9. is a graph illustrating the release of Ketotifen fumarate from the hydrogel film of Example 46 and Example 47.

Active loading of ketotifen in hydrogel film of Example 26 and Example 31 after 24 h of imbibition is shown in Table 12. Release of the drug was tested by immersing the drug loaded film in 2 ml of phosphate buffered saline (PBS) (pH=7.4). An aliquot of 0.5 ml of the solution was sampled and replaced with fresh solution at predetermined intervals. The amount of drug released in the media was measured using HPLC techniques. Cumulative and its normalized drug concentration was calculated and plotted as a function of respective time of sampling which shows a gradual release for a long period of time (>24 hours) as shown in FIG. 9. Total percentage release of the ketotifen after 48 h is listed below in the table.

TABLE 12

Uptake and percentage release of Ketotifen fumarate

| Example | Uptake (ppm) | % release |
|---|---|---|
| Example 26 | 1614 | 38 |
| Example 31 | 522 | 96 |

It is quite evident from the drug uptake values that drug loading in hydrogel film incorporated with ionic monomer is higher as compared to the non-functional hydrogel film, without compromising film properties. Higher drug loading increases the residence time and bioavailability of drugs within therapeutic levels on the ocular surface.

Functional drugs present in ionic form can bound to the ionic moieties present in the hydrogel film as in Example 26 and release the drug in a sustainable manner. The sustained drug concentration in the tear fluid is proportional to the loading capacity of the film.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The foregoing description identifies various, non-limiting embodiments of an ionically modified silicone having an overall net neutral charge and compositions and materials comprising the same. Modifications may occur to those skilled in the art and to those who may make and use the invention. The disclosed embodiments are merely for illustrative purposes and not intended to limit the scope of the invention or the subject matter set forth in the claims.

What is claimed is:
1. A silicone compound of the Formula (I):

where $R^1$ is chosen from a chemical bond or a divalent group comprising 1 to 16 carbon atoms optionally containing a heteroatom chosen from oxygen, sulfur, or nitrogen;
$R^2$ is a linear, branched, cyclic, or cage like siloxanyl moiety, or a silane moiety having the general structure (a)

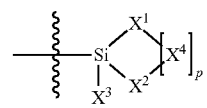

$X^1$ is independently selected from linear or branched alkyl group containing 1-16 carbon atoms, trimethoxy silyl, trimethylsilyloxy, —O[Si(CH$_3$)$_2$O-]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si(CH$_3$)$_2$O—, or (CH$_3$)$_3$Si(CH$_2$CH$_2$Si(CH$_3$)$_2$O)$_s$— wherein s is an integer chosen from 0-200;
$X^2$ is independently selected from a linear or branched alkyl group containing 1-16 carbon atoms, trimethoxy silyl, trimethylsilyloxy, —O[Si(CH$_3$)$_2$O-]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si $(CH_3)_2O-$, or $(CH_3)_3Si(CH_2CH_2Si(CH_3)_2O)_z-$ wherein z is an integer chosen from 0-200, or $-[OSi(CH_3)_2]mG^1$, wherein $G^1$ is $(CH_3)_3SiO-$ and m is an integer from 0 to 400, or a reactive or non-reactive silicone group with the general Formula (b1) or (b2):

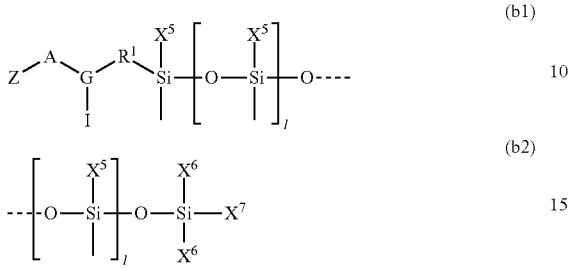

where l is an integer chosen from 0-200; and p in Formula (a) is 0 when $X^2$ is of the Formula (b1) or (b2);

$X^3$ and $X^5$ are independently chosen from a C1-C6 alkyl, trimethylsiloxy, trimethylsilyloxy, $(CH_3)_3SiCH_2CH_2-$, $(CH_3)_3SiCH_2CH_2Si(CH_3)_2O-$, and $OSi(CH_3)_2$, with the provisos that (i) when $X^1$ or $X^6$ is $-O[Si(CH_3)_2O-]_n$, then $X^3$ and $X^5$, respectively, is $OSi(CH_3)_2$ and $X^1$ forms a chemical bond with the $X^3$ and $X^5$ forms a chemical bond with $X^6$ to correspondingly form a divalent $-X^1-X^3-$ or $X^5-X^6-$ group, which is bonded to the silicon atom to form a cyclic polysiloxane ring, and (ii) when $X^3$ and/or $X^5$ is $-OSi(CH_3)_2$, then $X^1$ and/or $X^6$ is $-O[Si(CH_3)_2O-]_n$, and $X^1$ forms a chemical bond with the $X^3$ and/or $X^5$ forms a chemical bond with $X^6$ to form a divalent $-X^1-X^3-$ or $X^5-X^6-$ group, which is bonded to the silicon atom to form a cyclic polysiloxane ring;

where, $X^1$, $X^2$ and $X^3$ optionally can each be $-O[Si(R^7)O-]_n$, and interconnected to form a polysilsesquioxane ring as described in formula (b3) and $R^7$ is independently chosen from a linear or branched alkyl or aralkyl group;

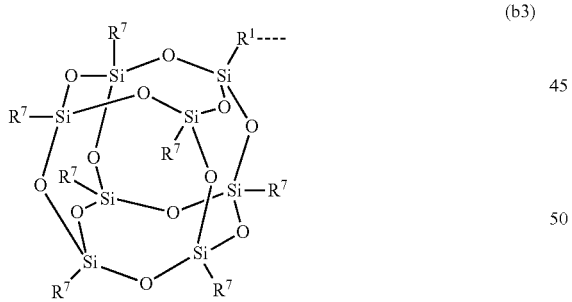

$X^6$, $X^7$, and $X^8$ are independently chosen from a linear or branched alkyl group containing 1-16 carbon atoms, alkoxy, trimethylsilyloxy, or $-O[Si(CH_3)_2O-]_n$, wherein n is an integer chosen from 1 to 9, and wherein $X^6$ and $X^7$, $X^7$ and $X^8$, or $X^6$ and $X^8$ may form a ring;

$X^4$ is an optional connecting group selected independently from dimethylsiloxy, $-O[Si(CH_3)_2O-]$, or $-CH_2CH_2(CH_3)_2SiO$-moiety;

p is an integer chosen from 0-10;

G is a bridging unit between the siloxane moiety and reactive moiety independently selected from a linear or branched alkyl group or a carbocyclic group optionally contains hetero atoms;

A is a heteroatom;

I is an ionic containing moiety with 0-200 carbon atoms optionally containing heteroatoms, and is of the formula:

$$K-L-M(X)_w$$

wherein K is a divalent hetero atom, and in one embodiment K is an oxygen atom,

L is a chemical bond or a divalent hydrocarbon radical comprising a substituted or unsubstituted, linear or branched, aliphatic or aromatic hydrocarbon with 0-50 carbon atoms, which may optionally contain heteroatoms;

w is 1 to 10;

M is independently chosen from:

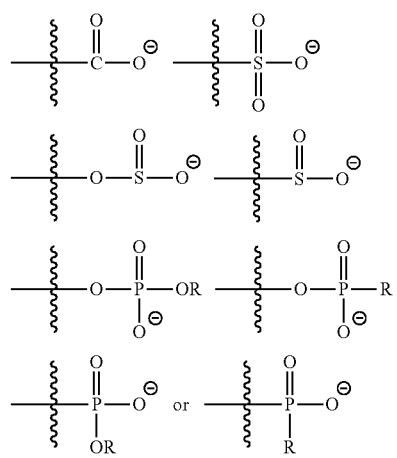

X is independently chosen from a quaternary ammonium compound, a quaternary ammonium group forming compound, a cationic polymer, a group 15 elements chosen from N, P, As, Sb, or Bi, a metal, an alkali metal, an alkaline earth metal, a transition metal, a rare-earth metal or a combination of two or more thereof;

and R is independently selected from hydrogen, an alkyl, an aryl, an aralkyl, and a cycloaliphatic with 1-100 carbon atoms with optional heteroatoms which may contain functional groups like hydroxy, amide, urethane, urea, ester, amine, thiol, disulfide, ether, and the formula

wherein $G^1$ is an alkyl, an aryl, an aralkyl, and a cycloaliphatic with 1-100 carbon atoms with optional heteroatoms;

$Z^1$ is a reactive or non-reactive functional moiety of formula (C1)

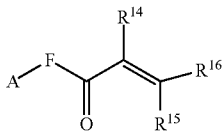

wherein $R^{14}$, $R^{15}$, and $R^{16}$ are independently chosen from hydrogen or monovalent hydrocarbon radical with 1-5 carbon atoms; and F is a linker group chosen from aliphatic, cycloaliphatic, or aromatic hydrocarbon radical having 1-16 carbon atoms and optionally containing a heteroatom; and A is chosen from none or a heteroatom; and $R^1$ and $R^2$ are as defined above and x is 0-10; and Z is a polymerizable group having the general Formula (c):

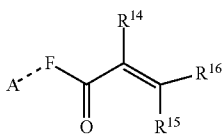
(c)

wherein $R^{14}$, $R^{15}$, and $R^{16}$ are independently chosen from hydrogen or monovalent hydrocarbon radical with 1-5 carbon atoms; and F is a linker group chosen from aliphatic, cycloaliphatic, or aromatic hydrocarbon radical having 1-16 carbon atoms and optionally containing a heteroatom.

2. The compound of claim 1, wherein X is independently chosen from

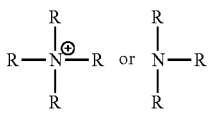

where R is independently selected from hydrogen, an alkyl, an aryl, an aralkyl, and a cycloaliphatic with 1-100 carbon atoms with optional heteroatoms which may contain functional groups like hydroxy, amide, urethane, urea, ester, amine, thiol, disulfide, ether, and the formula (i):

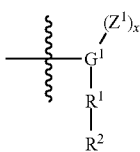
(i)

wherein $G^1$ is an alkyl, an aryl, an aralkyl, and a cycloaliphatic with 1-100 carbon atoms with optional heteroatoms;

$Z^1$ is a reactive or non-reactive functional moiety of formula

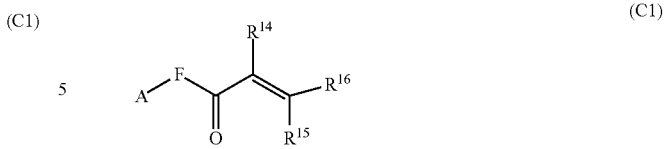
(C1)

wherein $R^{14}$, $R^{15}$, and $R^{16}$ are independently chosen from hydrogen or monovalent hydrocarbon radical with 1-5 carbon atoms; and F is a linker group chosen from aliphatic, cycloaliphatic, or aromatic hydrocarbon radical having 1-16 carbon atoms and optionally containing a heteroatom; and A is chosen from none or a heteroatom; and $R^1$ and $R^2$ are as defined in claim 1 and x is 0-10.

3. The compound of claim 1, wherein X is a cationic polymer chosen from, a poly(ethylene amine), a poly(pyridine), a poly(imidazolium), a poly-acrylate based quaternary ammonium salt, or a combination of two or more thereof.

4. The compound of claim 1, wherein K is oxygen, L is a C1-C6 divalent hydrocarbon radical, and M is —C(O)—OH.

5. A composition comprising (A) a hydrogel material and (B) an active substance, wherein the hydrogel material (A) is formed from a reaction mixture comprising the silicone compound of claim 1.

6. The composition of claim 5 wherein the reaction mixture from which the gel material (A) is formed comprises an organic monomer, which is chosen from a vinylic monomer, an acrylamide monomer, an acrylic monomer, or a combination of two or more thereof.

7. The composition of claim 6, wherein (a) the vinylic monomer is chosen from N-vinyl-pyrrolidone, N-vinyl-caprolactam, N-vinyl-acetamide, N-vinyl-formamide, N-vinyl-isopropylamide, vinyl benzene, vinyl naphthalene, vinyl pyridine, vinyl alcohol, vinyl containing silicone, or a combination of two or more thereof (b) the acrylic monomer is chosen from 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-dimethylacrylamide, N-isopropylacrylamide, acrylamide, methacrylamide, acrylic acid, methacrylic acid, acrylated hydrophilic or hydrophobic organo-silicone, or a combination of two or more thereof.

8. The composition of claim 5, wherein the reaction mixture from which the hydrogel material (A) is formed further comprises (i) optionally an active ingredient that is reactive or non-reactive to actinic curing conditions; and (ii) optionally, an organic monomer, an organic macromer, a reactive polymer, a cross-linker, a compatibilizer, a tinting agent, an initiator, or a combination of two or more thereof.

9. The composition of claim 8, wherein the silicone compound of Formula (I) is present in an amount of from about 1 weight percent to about 99 weight percent of the composition.

10. The composition of claim 5, wherein the ratio of the silicone compound of Formula (I) to organic monomer is about 1:99 to 99:1.

11. The composition of claim 5, wherein the active substance (B) is chosen from an agent affecting the central nervous system, an antiallergic agent, a cardiovascular agent, an agent affecting respiratory organs, an agents affecting digestive organ, hormone preparations, an agent affecting metabolism, an antitumor agent, an antibiotic preparation, a chemotherapeutic, an antimicrobial, a local anesthetic, an antihistaminic, antiphlogistic, an astringent, an ophthalmically-active drug, a vitamin, an antifungal agent, a peripheral nervous anesthetic, a vasodilator, a crude drug essence, a tincture, a crude drug powder, a hypotensive agent, an immunosuppressant, a lubricating agent, a wetting agent or a combination of two or more thereof.

12. The composition of claim 11, wherein the ophthalmically active drug is chosen from pilocarpine, epinephrine, tetracycline, phenylephrine, eserine, phospholine iodide, demecarium bromide, cyclopentolate, homatropine, scopolamine, chlortetracycline, bacitracin, neomycin, polymixin, gramicidin, oxytetracycline, chloramphenicol, gentamycin, penicillin, erythromycin, carbachol, sulfacetamide, polymixin B, idoxuridine, isoflorophate, fluoromethalone, dexamethasone, hydrocortisone, hydrocortisone acetate, dexamethasone 21-phosphate, fluorocinolone, medrysone, prednisolone, methyl prednisolone, prednisolone 21-phosphate, prednisolone acetate, betamethasone, Ibuprofen, Flurbiprofen, Cloricromene, Diclofenac diethyl ammonium, Piroxicam, Methylprednisolonem, triamcinolone, timolol maleate, ketotifen fumarate, moxifloxacin hydrochloride monohydrate or a combination of two or more thereof.

13. A gel formed from the composition of any of claim 5.

14. The gel of claim 13, wherein the gel is in the form of a film.

15. A hydrogel formed from the composition of claim 5.

16. The hydrogel of claim 15, wherein the hydrogel comprises an active ingredient.

17. The hydrogel of claim 15 in the form of a contact lens.

18. A contact lens comprising the hydrogel of claim 15.

19. An actives delivery system comprising the hydrogel of claim 15.

20. The actives delivery system of claim 19, wherein the hydrogel material is a hydrogel film.

21. The actives delivery system of claim 19, wherein the hydrogel material is in the form of a contact lens.

22. A contact lens comprising the actives delivery system of claim 19.

23. A medical device comprising the actives delivery system of claim 19 disposed on a surface thereof.

24. The medical device of claim 23, wherein the device is chosen from a probe, a wand, a film, a band, a patch, a contact lens, or an insert.

* * * * *